(12) United States Patent
Tracy et al.

(10) Patent No.: US 10,612,051 B2
(45) Date of Patent: Apr. 7, 2020

(54) METHOD OF PRODUCING BIOPRODUCTS

(71) Applicant: White Dog Labs, Inc., New Castle, DE (US)

(72) Inventors: Bryan P. Tracy, Wilmington, DE (US); Christopher Joseph McWilliams, Somerville, MA (US); Aharon M. Eyal, Jerusalem (IL)

(73) Assignee: WHITE DOG LABS, INC., New Castle, DE (US)

( * ) Notice: Subject to any disclaimer, the term of this patent is extended or adjusted under 35 U.S.C. 154(b) by 0 days.

(21) Appl. No.: 15/563,190

(22) PCT Filed: Mar. 29, 2016

(86) PCT No.: PCT/US2016/024724
§ 371 (c)(1),
(2) Date: Sep. 29, 2017

(87) PCT Pub. No.: WO2016/160812
PCT Pub. Date: Oct. 6, 2016

(65) Prior Publication Data
US 2018/0087075 A1 Mar. 29, 2018

Related U.S. Application Data

(60) Provisional application No. 62/140,961, filed on Mar. 31, 2015.

(51) Int. Cl.
| | | |
|---|---|---|
| *C12P 7/52* | (2006.01) |
| *C07C 29/86* | (2006.01) |
| *C07C 45/80* | (2006.01) |
| *C07C 51/48* | (2006.01) |
| *C12P 7/16* | (2006.01) |
| *C07D 307/50* | (2006.01) |
| *B01D 11/00* | (2006.01) |
| *B01D 11/02* | (2006.01) |
| *C07C 67/58* | (2006.01) |
| *C12P 7/26* | (2006.01) |
| *C12P 7/44* | (2006.01) |
| *C12P 7/04* | (2006.01) |

(52) U.S. Cl.
CPC ............... *C12P 7/52* (2013.01); *B01D 11/00* (2013.01); *B01D 11/02* (2013.01); *C07C 29/86* (2013.01); *C07C 45/80* (2013.01); *C07C 51/48* (2013.01); *C07C 67/58* (2013.01); *C07D 307/50* (2013.01); *C12P 7/04* (2013.01); *C12P 7/16* (2013.01); *C12P 7/26* (2013.01); *C12P 7/44* (2013.01); *Y02E 50/10* (2013.01)

(58) Field of Classification Search
None
See application file for complete search history.

(56) References Cited

U.S. PATENT DOCUMENTS

| | | |
|---|---|---|
| 3,018,308 A | 1/1962 | Levine et al. |
| 3,950,442 A | 4/1976 | Vogel et al. |
| 4,377,638 A | 3/1983 | Bryant et al. |
| 4,469,905 A | 9/1984 | Inwood et al. |
| 4,482,768 A | 11/1984 | Somekh |
| 4,508,928 A | 4/1985 | Victor |
| 4,761,505 A | 8/1988 | Diana et al. |
| 4,827,046 A | 5/1989 | Harandi et al. |
| 4,877,530 A | 10/1989 | Moses et al. |
| 4,956,052 A | 9/1990 | Hirata et al. |
| 4,981,491 A | 1/1991 | Harandi et al. |
| 5,009,859 A | 4/1991 | Harandi et al. |
| 5,041,690 A | 8/1991 | Harandi et al. |
| 5,047,070 A | 9/1991 | Harandi et al. |
| 5,064,623 A | 11/1991 | Harandi et al. |
| 5,130,101 A | 7/1992 | Harandi et al. |
| 5,144,085 A | 9/1992 | Harandi et al. |
| 5,167,937 A | 12/1992 | Harandi et al. |
| 5,387,721 A | 2/1995 | Kruse et al. |
| 5,763,693 A | 6/1998 | Hirata et al. |
| 8,088,958 B2 | 1/2012 | Schucker |
| 2009/0171129 A1 | 7/2009 | Evanko et al. |
| 2010/0069686 A1 | 3/2010 | Waibel et al. |
| 2011/0136193 A1 | 6/2011 | Grady et al. |
| 2011/0300597 A1* | 12/2011 | Burk ..................... C12N 15/52 435/167 |
| 2013/0210104 A1 | 8/2013 | Pearlman et al. |
| 2014/0066669 A1 | 3/2014 | Schonemann et al. |
| 2014/0303408 A1 | 10/2014 | Zaher |
| 2015/0211024 A1* | 7/2015 | Garcez Lopes ........ C12N 15/52 435/145 |
| 2018/0087023 A1 | 3/2018 | Tracy et al. |

FOREIGN PATENT DOCUMENTS

| | | |
|---|---|---|
| WO | 2013/175380 | 11/2013 |
| WO | WO-2014/036140 A2 * | 3/2014 |
| WO | 2014/144643 | 9/2014 |
| WO | 2015/134246 | 9/2015 |

OTHER PUBLICATIONS

Treybal, Robert E., "Liquid Extraction", McGraw-Hill, New York, 1951.

(Continued)

*Primary Examiner* — Iqbal H Chowdhury
(74) *Attorney, Agent, or Firm* — Greenblum & Bernstein, P.L.C.

(57) ABSTRACT

Methods for production of a bioproduct with a microorganism and selective extraction of bioproducts from a fermentation broth. The methods may include mixing a carbon source, a nitrogen source, and an extractant-depleted raffinate to form a fermentation medium, and fermenting the medium with a microorganism to form a fermentation broth having at least one bioproduct. The bioproduct may be extracted from the fermentation broth with an extractant comprising an olefin to form an extract and a raffinate, and the extract may be further separated from the raffinate. The bioproduct may then be separated from the extract, and the extractant may be separated from the raffinate to regenerate the extract-depleted raffinate.

21 Claims, No Drawings

(56) References Cited

OTHER PUBLICATIONS

"Perry's Chemical Engineering Handbook", Chapter 15, 8th Edition, 2008.
Petre, "Kinetic investigation on direct hydration of n-butene in a multiphase reactor", Ph.D. Thesis [online], retrieved from the internet <http://www.gbv.de/dms/clausthal/E_DISS/2006/db108394.pdf>, May 9, 2006.
Munson et al., "Factors Influencing Solvent Selection for Extraction of Ethanol from Aqueous Solutions," *Ind. Eng. Chem. Process Des. Dev.*, vol. 23, No. 1, pp. 109-115, 1984 (Abstract).
Mahajani et al., "Reactive Distillation," *The Academic Press*, pp. 4075-4082, 2000.
International Search Report issued in PCT/US2016/024730, dated Jun. 29, 2016.
International Preliminary Report on Patentability issued in PCT/US2016/024730, dated Oct. 12, 2017.
International Search Report issued in PCT/US2016/024724, dated Jul. 27, 2016.
International Preliminary Report on Patentability issued in PCT/US2016/024724, dated Oct. 12, 2017.
U.S. Appl. No. 62/140,969, filed Mar. 31, 2015.
U.S. Appl. No. 62/140,961, filed Mar. 31, 2015.
Extended European Search Report issued in EP Patent Application No. 16774003.4, dated Sep. 27, 2018.
Shaima Nahreen, "Catalytic Upgrading of Biomass Fermentation Products and Bio-methane to Energy Dense Hydrocarbon Fuels", Auburn University, Alabama, USA, dissertation, May 10, 2015, pp. 1-182, XP002784917.
Shaohua Zheng et al., Feasibility of bio-based lactate esters as extractant for biobutanol recovery: (Liquid + Liquid) equilibria, J. Chem. Thermodynamics 93, 2016, pp. 127-131.
European search Report issued with respect to Application No. 16774001.8, dated Oct. 10, 2018.

* cited by examiner

METHOD OF PRODUCING BIOPRODUCTS

CROSS REFERENCE TO RELATED APPLICATION

The instant application claims priority to U.S. Provisional Application No. 62/140,961, filed Mar. 31, 2015, the disclosure of which is incorporated by reference herein in its entirety.

FIELD

Provided are methods for the production of biomolecules with a microorganism, which methods include selective extraction of the biomolecules from, for example, a fermentation broth.

BACKGROUND

The notion of using a microorganism to produce a biomolecule such as butanol has been pursued. For example, US 2014/0303408 discloses methods for recovering butanol from a fermentation medium comprising the use of a water immiscible organic extractant comprising a dry solvent such as a C7 to C22 hydrocarbon and a specialized recombinant yeast. However, previous methods of generating bioproducts have been energetically or economically inefficient, and/or require the use of specialized reagents/microorganisms that make performing the method difficult or expensive.

SUMMARY

In one aspect, provided is a method for producing a bioproduct comprising: (i) mixing a carbon source and a nitrogen source to form a fermentation medium; (ii) fermenting said medium with a microorganism to form a fermentation broth containing at least one bioproduct; (iii) extracting at least a fraction of said fermentation broth with an extractant comprising an olefin to form an extract and a raffinate, wherein both extract and raffinate comprise said extractant, said bioproduct, and water; and wherein the boiling point of said olefin at atmospheric pressure is under 10° C.; (iv) separating said extract from said raffinate; (v) separating at least a fraction of the bioproduct from said extract; and (vi) separating at least a fraction of said extractant from said raffinate to generate an extractant-depleted raffinate.

In an embodiment, also provided is a method as described above, wherein said fermentation medium further comprises at least a fraction of an extractant-depleted raffinate.

In an embodiment, also provided is a method as described above, wherein said bioproduct is selected from the group consisting of butanol, ethanol, acetone, alcohols, carboxylic acids, hydroxycarboxylic acids, dicarboxylic acids, furfurals, ketones, aldehydes, esters, lactones, lipids, glycolipids, carotenoids, polysaccharides and combinations thereof.

In an embodiment, also provided is a method as described above, wherein said bioproduct is butanol. For example, provided is such a method, wherein said butanol is n-butanol. Also provided is such a method, wherein said butanol is crotyl alcohol.

In another embodiment, also provided is a method as described above, wherein said bioproduct is butyric acid.

In an embodiment, also provided is a method as described above, wherein said olefin is selected from the group consisting of 1-butene, 2-butene, and iso-butene.

In an embodiment, also provided is a method as described above, wherein said fermentation medium further comprises said extractant.

In an embodiment, also provided is a method as described above, wherein said fermentation broth contains at least two bioproducts, at least one of which is selected from the group consisting of ethanol, acetone, isopropanol, and a carboxylic acid.

In an embodiment, also provided is a method as described above, wherein the concentration of said bioproduct in said fermentation broth is less than about 5 weight (wt) %.

In an embodiment, also provided is a method as described above, wherein said fermentation broth contains cell mass during said extracting.

In an embodiment, also provided is a method as described above, wherein said extractant further comprises at least one of dimethyl ether, methyl-ethyl ether, and diethyl ether.

In an embodiment, also provided is a method as described above, wherein the weight ratio between bioproduct and water in said extract is at least about 5 times greater than said ratio in said fermentation broth.

In an embodiment, also provided is a method as described above, wherein the weight ratio between bioproduct and water in said extract is greater than said ratio in a saturated aqueous solution of said bioproduct at the same temperature.

In an embodiment, also provided is a method as described above, for example, wherein both said fermentation broth and said extract contain a second bioproduct selected from the group consisting of ethanol, isopropanol and acetone. Also provided is such a method, wherein both said fermentation broth and said extract comprise a second bioproduct, and wherein the weight ratio between said bioproduct and said second bioproduct in said extract is at least about 2 times greater than said ratio in said fermentation broth.

In an embodiment, also provided is a method as described above, wherein both said fermentation broth and said extract contain a carbon source, and wherein the weight ratio between said bioproduct and said carbon source in said extract is at least about 10 times greater than said ratio in said fermentation broth.

In an embodiment, also provided is a method as described above, wherein both said fermentation broth and said extract contain a nitrogen source, and wherein the weight ratio between said bioproduct and said nitrogen source in said extract is at least about 10 times greater than said ratio in said fermentation broth.

In an embodiment, also provided is a method as described above, wherein said extracting is conducted in a countercurrent column, wherein the extractant to fermentation broth flux ratio is in the range between 0.5 and 5, and wherein at least about 80% of the bioproduct in said fermentation broth is extracted. Also provided such a method, wherein said fermentation broth contains a second bioproduct, wherein said extracting further comprises extracting a fraction of said second bioproduct, and wherein the extracted fraction of said second bioproduct is smaller than the fraction of extracted bioproduct.

In an embodiment, also provided is a method as described above, wherein separating at least a fraction of the bioproduct from said extract comprises separating at least a fraction of said extractant from said extract to form an extractant-depleted bioproduct solution. Also provided is such a method, wherein the weight ratio between said bioproduct and water in said extractant-depleted bioproduct solution is at least about 5 times greater than said ratio in said fermentation broth. Also provided is such a method, wherein the weight ratio between bioproduct and water in said extractant-depleted bioproduct solution is greater than said ratio in a saturated aqueous solution of said bioproduct at the same temperature. Also provided is such a method, further comprising liquefying at least a fraction of the separated extractant with a refrigerant in a refrigerant circuit. In an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

In an embodiment, also provided is a method as described above, wherein said microorganism is viable in a fermentation broth comprising said extractant at a concentration of at least about 0.01 g/L (grams per liter).

In an embodiment, also provided is a method as described above, wherein said microorganism is a member of the phylum Firmicutes.

In an embodiment, also provided is a method as described above, wherein said microorganism is a member of the class Clostridia.

In an embodiment, also provided is a method as described above, wherein said microorganism is a member of the genus *Eubacterium*.

In an embodiment, also provided is a method as described above, wherein said microorganism is a *Eubacterium limosum*.

In an embodiment, also provided is a method as described above, wherein said microorganism is a member of the genus *Clostridium*. Also provided is such a method, wherein said microorganism is a *Clostridium* selected from the group consisting of *Clostridium butyricum, Clostridium acetobutylicum, Clostridium saccharoperbutylacetonicum, Clostridium beijerickii, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum,* and *Clostridium autoethanogenum*.

In an embodiment, also provided is a method as described above, for example, wherein said fermentation medium further comprises at least one of ethanol, acetone, isopropanol, and a carboxylic acid, and wherein said carboxylic acid is selected from the group consisting of acetic acid, butyric acid, and lactic acid.

In an embodiment, also provided is a method as described above, wherein said extractant-depleted raffinate contains a carbon source and a nitrogen source.

In an embodiment, also provided is a method as described above, wherein said carbon source comprises liquefied corn, the fermentation broth additionally contains wet solids, and the method further comprises separating at least a fraction of wet solids from said fermentation broth. Also provided is such a method, further comprising contacting wet solids that have been separated from said fermentation broth with a fraction of said extractant-depleted raffinate to form a mixture and separating bioproduct from said mixture to form a bioproduct-depleted residue.

In another aspect, provided is a method for producing n-butanol comprising: (i) mixing a carbon source, a nitrogen source, and an extractant-depleted raffinate to form a fermentation medium; (ii) fermenting said medium with an n-butanol-producing microorganism to form a fermentation broth containing n-butanol as a first bioproduct at a concentration of less than about 5 wt % and at least one second bioproduct selected from the group consisting of acetone, ethanol, isopropanol, and a carboxylic acid; (iii) extracting at least a fraction of said fermentation broth with an extractant comprising an olefin to form an extract and a raffinate, wherein both extract and raffinate comprise said extractant, n-butanol, said second bioproduct, and water; and wherein the boiling point of said olefin at atmospheric pressure is under 10° C.; (iv) separating said extract from said raffinate; (v) separating at least a fraction of the n-butanol from said extract; and (vi) separating at least a fraction of said extractant from said raffinate to regenerate the extractant-depleted raffinate.

In an embodiment, also provided is such a method, wherein the weight ratio between n-butanol and water in said extract is at least about 5 times greater than said ratio in said fermentation broth.

In an embodiment, also provided is such a method, wherein the weight ratio between n-butanol and water in said extract is greater than said ratio in a saturated aqueous solution of n-butanol at the same temperature.

In an embodiment, also provided is such a method, wherein said extractant-depleted raffinate comprises a carbon source, a nitrogen source, and a carboxylic acid. Also provided is such a method, wherein said carboxylic acid is selected from the group consisting of acetic acid, butyric acid and lactic acid.

In another aspect, provided is a method for producing crotyl alcohol comprising: (i) mixing a carbon source, a nitrogen source, and an extractant-depleted raffinate to form a fermentation medium; (ii) fermenting said medium with a crotyl alcohol-producing microorganism to form a fermentation broth containing crotyl alcohol as a first bioproduct at a concentration of less than about 5 wt % and at least one second bioproduct selected from the group consisting of acetone, ethanol, isopropanol and a carboxylic acid; (iii) extracting at least a fraction of said fermentation broth with an extractant comprising an olefin to form an extract and a raffinate, wherein both extract and raffinate comprise said extractant, crotyl alcohol, said second bioproduct, and water; and wherein the boiling point of said olefin at atmospheric pressure is under 10° C.; (iv) separating said extract from said raffinate; (v) separating at least a fraction of the crotyl alcohol from said extract; and (vi) separating at least a fraction of said extractant from said raffinate to regenerate the extractant-depleted raffinate.

In an embodiment, also provided is such a method, wherein the weight ratio between crotyl alcohol and water in said extract is at least about 5 times greater than said ratio in said fermentation broth.

In an embodiment, also provided is such a method, wherein the weight ratio between crotyl alcohol and water in said extract is greater than said ratio in a saturated aqueous solution of crotyl alcohol at the same temperature.

In an embodiment, also provided is such a method, wherein said extractant-depleted raffinate comprises a carbon source, a nitrogen source, and a carboxylic acid. Also provided is such a method, wherein said carboxylic acid is selected from the group consisting of acetic acid, butyric acid, and lactic acid.

DETAILED DESCRIPTION

Definitions

As used herein, the term "carbohydrate composition" refers to any composition comprising at least one carbohydrate, including aqueous solutions, solids and slurries.

As used herein, the term "carbon source" refers to any composition comprising at least one of a carbohydrate composition, glycerol, methanol, CO2, and CO.

As used herein, the term "nitrogen source" refers to compounds or compositions that may be used to supply an organism with nitrogen during fermentation.

As used herein, the term "extractant" refers to an organic liquid with limited solubility in water, e.g. less than 50% solubility at 25° C.

As used herein, the term "extractant olefin" or "olefin" refers to an olefin used as an extractant.

As used herein, "contacting with extractant" "extracting" and "liquid-liquid extraction" interchangeably refer to contacting an aqueous solution or an aqueous slurry with an extractant, whereby a solute in the aqueous solution or slurry transfers (is extracted) to the extractant phase.

As used herein, the term "extract" refers to an extractant-rich phase generated during extraction, which phase comprises said extracted solute.

As used herein, the term "raffinate" refers to the solute-depleted aqueous solution or slurry generated during extraction.

As used herein, the term "extractant to fermentation broth flux ratio" and "flux ratio" interchangeably refer to the ratio between the weight fluxes of the extractant and the fermentation broth.

As used herein, the term "butanol" refers to any 4-carbon compound carrying at least one hydroxyl group. Examples of butanol include n-butanol, iso-butanol, 2-butanol, tert-butanol, crotyl alcohol, 1,4 butanediol, 2,3 butanediol, and combinations thereof.

As used herein, the term "liquefied corn" refers to corn kernels treated with hot water and starch-hydrolyzing enzymes.

As used herein, the term "distribution coefficient" refers to the ratio between the concentration of a solute in an organic phase and its concentration in an aqueous phase, while those phases are in equilibrium.

As used herein, the term "selectivity" refers to the ratio between distribution coefficients of two solutes.

As used herein, the term "extraction yield" means the extent of extraction as calculated by dividing the amount of a solute in the extract by the amount of that solute in the extracted solution.

As used herein, the term "carboxylic acid" includes both free and salt form carboxylic acids.

As used herein, the term "vaporizing" refers to transferring from a liquid phase into a vapor phase, e.g. by temperature elevation, pressure reduction, bubbling a gas, or combinations thereof.

As used herein, the term "condensing" refers to transferring from a vapor phase to a liquid phase, e.g. by temperature reduction, pressure elevation, or combinations thereof.

As used herein, the terms "fermenting" refers to a process in which a microorganism is cultivated in a fermentation medium containing raw materials, such as feedstock and nutrients, wherein the microorganism converts raw materials, such as a feedstock, into products.

As used herein, the term "fermentation medium" refers to a composition containing a carbon source (e.g., a carbohydrate), a nitrogen source and optionally other nutrients in which fermentation takes place.

As used herein, the term "fermentation broth" refers to the fermentation medium post fermentation, as such or after removal of biomass therefrom.

As used herein, the term "inhibition", when referring to an organism, refers to restraining any portion of the life cycle or metabolic activity of the organism.

As used herein, the term "growth inhibition" refers to the inhibition of cell division. Cell division increases the cell population count.

As used herein, the term "solventogenesis inhibition" refers to inhibition of the cell's metabolic activity during the portion of the organism population's life cycle phase in which product and coproduct production is occurring.

As used herein, the terms "coproduct" refers to a biomolecule generated during the fermentation concurrently with the bioproduct.

As used herein, the term "bioproduct" refers to any molecule generated by a living organism in the fermentation, which includes proteins, polysaccharides, lipids, nucleic acids, and primary or secondary metabolites.

Unless indicated otherwise, percent is weight percent and ratio is weight ratio. Unless indicated otherwise, weight ratio means the ratio between weight content, e.g. in an aqueous solution containing 20% solute and 80% water, the solute to water weight ratio is 20:80 or 1:4.

A First Embodiment

According to a first aspect, provided is a method for producing a bioproduct, comprising: (i) mixing a carbon source and a nitrogen source to form a fermentation medium; (ii) fermenting said medium with a microorganism to form a fermentation broth comprising at least one bioproduct; (iii) extracting at least a fraction of said fermentation broth with an extractant comprising an olefin to form an extract and a raffinate, wherein both extract and raffinate comprise said extractant, said bioproduct, and water; and wherein the boiling point of said olefin at atmospheric pressure is under 10° C.; (iv) separating said extract from said raffinate; (v) separating at least a fraction of the bioproduct from said extract; and (vi) separating at least a fraction of said extractant from said raffinate to generate an extractant-depleted raffinate.

According to an embodiment, said fermentation medium may comprise an extractant-depleted raffinate. In an embodiment the fermentation medium comprises at least a fraction of said extractant-depleted raffinate, e.g. at least 50 wt %, at least 60 wt %, at least 70 wt %, at least 80 wt %, or at least 90 wt %.

Bioproducts

According to an embodiment, said bioproduct is one or more C3-C9 alcohols.

According to an embodiment, said bioproduct is one or more C3-C6 carboxylic acids, hydroxycarboxylic acids or dicarboxylic acids. According to a related embodiment, said one or more C3-C6 carboxylic acids or dicarboxylic acids are selected from the group consisting of propionic acid, butyric acid, lactic acid, malonic acid, fumaric acid, succinic acid, itaconic acid, levulinic acid, hexanoic acid, and 3-hydroxybutyric acid.

According to an embodiment, said bioproduct is one or more C2-C18 dicarboxylic acids. According to a related embodiment, said one or more C2-C18 dicarboxylic acids is selected from the group consisting of oxalic, propanedioic, butanedioic, pentanedioic, hexanedioic, heptanedioic, octanedioic, nonanedioic, decanedioic, undecanedioic, and dodecanedioic (DDDA).

According to an embodiment, said bioproduct is one or one or more C8-C18 fatty alcohols.

According to an embodiment, said bioproduct is one or one or more butadienes. According to a related embodiment, said one or more butadienes are selected from the group consisting of butadiene and 2-methyl-1,3-butadiene (isoprene).

According to an embodiment, said bioproduct is one or more furfurals. According to a related embodiment, said one or more furfurals is selected from the group consisting of furfural and hydroxymethylfurfural (5-(hydroxymethyl)-2-furalaldehyde).

According to an embodiment, said bioproduct is acetoin and/or furan. According to an embodiment, said bioproduct is a ketone, e.g. of more than 2 carbon atoms. According to an embodiment, said bioproduct is an aldehyde, e.g. of more than 2 carbon atoms. According to an embodiment, said bioproduct is lactone, including hydroxylated lactones, e.g. butyrolactone. According to an embodiment, said bioproduct is an ester. According to an embodiment, said bioproduct is a lipid, e.g. a monoglyceride, a diglyceride, a triglyceride, rhamnolipid or phospholipid. According to another embodiment, said bioproduct is a carotenoid, e.g. beta-carotene, astaxanthin, lutein or zeaxanthin. According to another embodiment, said bioproduct is a polysaccharide, e.g. xanthan gum.

According to various embodiments, said bioproduct has a solubility in water of less than about 15 wt % at 25° C.; has a carbon atom number to hydroxyl group ratio of 3 or greater and/or has a melting point of 100° C. or less.

According to an embodiment, said bioproduct is a butanol. According to an embodiment, said bioproduct is n-butanol. According to an embodiment, said bioproduct is crotyl alcohol. According to an embodiment, said bioproduct is butanediol. According to an embodiment, said bioproduct is butyric acid.

Fermentation Medium Formation

The method of the first aspect may comprise mixing a carbon source and a nitrogen source to form a fermentation medium. According to an embodiment, said fermentation medium further comprises at least a fraction of said extractant-depleted raffinate.

According to an embodiment, the carbon source is a carbohydrate composition. According to an embodiment, said carbohydrate composition comprises at least one hexose, such as glucose and fructose. Alternatively or additionally, said carbohydrate composition comprises at least one pentose, such as xylose or arabinose. Alternatively or additionally, said carbohydrate composition comprises at least one of disaccharides, tri-saccharides, oligosaccharides and polysaccharides. Examples of carbohydrate compositions containing polysaccharides include starch, cellulose and hemicellulose. Examples of carbohydrate compositions containing disaccharides include sucrose, sugarcane juice and sucrose-containing molasses. Suitable carbohydrate compositions include starchy crops, such as corn and wheat, sugarcane and sugar beet and lignocellulosic material. Suitable compositions also include algae and microalgae. Where desired, the carbohydrate compositions may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation.

According to an embodiment, said carbon source results from processing starch or a starch-comprising composition, e.g. corn kernels or wheat grains. According to an embodiment, said carbon source is liquefied corn. Alternatively or additionally, said carbon source results from processing cellulose or a cellulose-comprising composition.

According to an embodiment, the nitrogen source is selected from complex sources, such as corn steep liquor, yeast extract and stillage from ethanol production and components thereof, defined sources, such as ammonia, ammonium salts and urea and combinations thereof.

The method of the first aspect may include recycling extractant-depleted raffinate to form the fermentation medium of a next cycle. According to an embodiment, said extractant-depleted raffinate is a dilute aqueous solution, optionally comprising at least one of a carbon source, a nitrogen source, ethanol, acetone, isopropanol, a carboxylic acid and said olefin. According to an embodiment, said extractant-depleted raffinate comprises at least about 1.0 g/L (grams/liter) carbon source, at least 2 g/L or at least 3 g/L. According to an embodiment, said carboxylic acid is selected from the group consisting of acetic acid, butyric acid and lactic acid. According to an embodiment, said extractant-depleted raffinate comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L. According to an embodiment, said extractant-depleted raffinate comprises at least about 10 ppm (parts per million) of said olefin, at least 20 ppm or at least 30 ppm. According to another embodiment, it comprises less than about 500 ppm of said olefin, less than 400 ppm or less than 300 ppm.

According to the method of the first aspect, said carbon source, a nitrogen source and extractant-depleted raffinate are mixed to form the fermentation medium. According to an embodiment, said extractant-depleted raffinate is modified prior to said mixing. According to a related embodiment, modifying comprises at least one of vaporizing extractant comprised in it, temperature change, addition or removal of water, addition of another component, pH adjustment and heat treatment. According to an embodiment, said fermentation medium further comprises at least one of ethanol, acetone, isopropanol, a carboxylic acid and said olefin. According to an embodiment, said at least one of a carbon source, a nitrogen source, ethanol, acetone, isopropanol, a carboxylic acid and said olefin in said fermentation medium result from said extractant-depleted raffinate.

According to an embodiment, said fermentation medium comprises at least about 10 g/L carbon source at least 20 g/L or at least 30 g/L. According to another embodiment, it comprises less than about 500 g/L carbon source, less than 400 g/L or less than 300 g/L.

According to an embodiment, said fermentation medium comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L.

According to an embodiment, said fermentation medium comprises at least about 10 ppm of said olefin, at least 20 ppm or at least 30 ppm. According to another embodiment, it comprises less than about 500 ppm of said olefin, less than 400 ppm or less than 300 ppm.

According to an embodiment, said fermentation medium comprises at least about 0.1 g/L ethanol at least 0.2 g/L or at least 0.5 g/L. According to another embodiment, it comprises less than about 50 g/L ethanol, less than 40 g/L or less than 30 g/L.

According to an embodiment, said fermentation medium comprises at least about 0.1 g/L acetone, at least 0.2 g/L or at least 0.5 g/L. According to another embodiment, it comprises less than about 50 g/L acetone, less than 40 g/L or less than 30 g/L.

Optionally, at least one of said carbon source, said extractant-depleted raffinate and said nitrogen source is treated prior to mixing, e.g., sterilized. Optionally, the product of mixing is further treated, e.g., combined with additional nutrients.

Fermenting

The method of the first aspect comprises fermenting said medium with a microorganism to form a fermentation broth comprising at least one bioproduct.

According to an embodiment, a fraction of the carbon source in the fermentation medium and optionally also part of the nitrogen source is consumed during said fermentation, resulting in the formation of said bioproduct and optionally a second bioproduct.

According to another embodiment, said fermentation medium also comprises a carboxylic acid and at least a fraction of said carboxylic acid is also assimilated.

According to an embodiment, said fermentation is conducted in a fermentor. According to an embodiment, said fermentation is conducted at a temperature between about 25° C. and about 45° C., or between about 30° C. and about 40° C. According to an embodiment, said fermentation also produces CO2. According to a related embodiment, said fermentation medium also comprises extractant olefin and a fraction of said olefin is removed from the fermentor along with vapors, e.g. CO2.

According to an embodiment, said microorganism is viable in a fermentation broth comprising said extractant olefin at a concentration greater than about 0.01 g/L, greater than 0.02 g/L or greater than 0.05 g/L; or butanol at a concentration greater than about 1.0 g/L, greater than 2 g/L or greater than 5 g/L; or ethanol at a concentration greater than about 1.0 g/L, greater than 2 g/L or greater than 5 g/L; or acetone at a concentration greater than about 1.0 g/L, greater than 2 g/L or greater than 5 g/L; or combinations thereof.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of bioproduct production, e.g., including without limitation microorganisms of the phylum Firmicutes, e.g., including without limitation Clostridia. Illustrative Clostridia include, e.g., *Clostridium* and *Eubacterium*. Illustrative members of the genus *Clostridium* include without limitation, *Clostridium butyricum, Clostridium acetobutylicum, Clostridium saccharoperbutylacetonicum, Clostridium saccharobutylicum, Clostridium beijerickii, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum, Clostridium autoethanogenum*. Illustrative *Eubacterium* include *Eubacterium limosum*.

Suitable bacteria and fungi also include those that are capable of hydrolyzing carbon sources and can be genetically engineered to produce said bioproduct. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus, Saccharomycopsis, Aspergillus, Pichia, Schwanniomyces* and *Polysporus*. The fungi may be able to perform the conversion aerobically or anaerobically. Examples of anaerobic fungi include, without limitation, *Piromyces* species (e.g., strain E2), *Orpinomyces* species (e.g. *Orpinomyces bovis*), *Neocallimastix* species (*N. frontalis*), *Caecomyce* species, *Anaeromyces* species and *Ruminomyces* species.

According to other embodiments, the microorganism is a temperature resistant microorganism. In other embodiments, the microorganism is an extractant resistant microorganism. The term "resistance" is defined as the property of a microorganism to have a low rate of growth inhibition and solventogenis inhibition in the presence of increasing concentrations of an inhibitor, such as an extractant, in the fermentation broth.

According to the method of the first aspect said fermentation forms a fermentation broth comprising at least one bioproduct. According to an embodiment, the concentration of said bioproduct in said fermentation broth is less than about 5 wt %, less than 4 wt %, less than 3 wt % or less than 2 wt %. According to an embodiment, the concentration of said bioproduct in said fermentation broth is in the range between about 0.5 wt % and about 5 wt % or between about 1 wt % and about 4 wt %.

According to some embodiments, the microorganism has a productivity of at least about 0.5 g/L per hour of bioproduct in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour.

According to an embodiment, said fermentation broth also comprises at least one second bioproduct, also referred to herein as a coproduct.

According to an embodiment, said second bioproduct is acetic acid.

According to an embodiment, said bioproduct is butanol and said second bioproduct is selected from the group consisting of ethanol, isopropanol, acetone, a carboxylic acid and their combinations.

According to an embodiment, said bioproduct is propionic acid and said second bioproduct is acetic acid.

According to an embodiment, said product is gamma-butyrolactone and said second bioproduct is 1,4-butanediol.

According to an embodiment, said product is butanol and said second bioproduct is 1,3-propanediol.

According to an embodiment, said product is hexanol and said second bioproduct is acetic acid.

Extracting

The method of the first aspect may comprise extracting at least a fraction of said fermentation broth with an extractant comprising an olefin to form an extract and a raffinate, wherein both extract and raffinate comprise said olefin, said bioproduct and water and wherein the boiling point of said olefin at atmospheric pressure is under 10° C. According to an embodiment, said extracting is conducted at a temperature greater than 10° C. According to an embodiment, said extracting is conducted at super-atmospheric pressure.

According to an embodiment, said olefin is an alkene. According to an embodiment, said olefin has the formula $C_4H_8$. According to an embodiment, said olefin is selected from the group consisting of 1-butene, 2-butene and isobutene.

According to an embodiment, said extracted fermentation broth comprises cell mass. According to this embodiment, cell mass is present in the fermentation broth during extraction.

According to an embodiment, said carbon source comprises liquefied corn, and the fermentation broth at the end of the fermentation comprises solids. According to an embodiment the method further comprises separating at least a fraction of the solids from said broth prior to said extracting. Any form of solids separation is suitable. According to an embodiment, said solids separation uses at least one of centrifugation and filtration.

According to an embodiment, said extractant comprises at least 70 wt %, 75 wt %, 80 wt %, 85 wt %, 90 wt % or at least 95 wt % olefin. According to an embodiment, said extractant further comprises at least one of dimethyl ether, methyl-ethyl ether and diethyl ether.

According to an embodiment, said extracting is conducted at a temperature between about 20° C. and about 50° C., between about 25° C. and about 45° C. or between about 30° C. and about 40° C. In various embodiments, extracting is conducted at about fermentation temperature. According to an embodiment, extraction is conducted in an extraction column and the temperature changes along the column.

In various embodiments, extracting is conducted at pressure between about 1.5 bar and about 10 bar, between about 2 bar and about 9 bar or between about 3 bar and about 8 bar.

According to an embodiment, extracting comprises mixing said fermentation broth with said extractant, followed by separating the generated extractant-rich phase (extract, typically the lighter phase) from the generated water-rich phase (raffinate, typically the heavier phase). Any form of mixing is suitable. Any form of phase separation is suitable. According to an embodiment, said extracting comprises multiple steps, e.g. between 2 and 30 stages, between 2 and 20 stages or between 2 and 10 stages. According to an embodiment, extracting is conducted counter-currently, also referred to as extracting in a counter-current mode. According to an embodiment, extracting is conducted in a series of mixer settlers, in an extraction column or in a centrifugal contactor.

According to varying embodiments, the flux ratio of extractant to broth is in the range of from about 0.2 to about 20, from about 0.3 to about 10, from about 0.4 to about 8, or from about 0.5 to about 3.

Methods for performing liquid-liquid extraction ("LLE") in a countercurrent column have been well documented in the literature, e.g., by Treybal, Robert E., "Liquid Extraction," McGraw-Hill, New York, 1951), which document is incorporated by reference herein in its entirety. Each countercurrent stage can be implemented with a mixer and settler. As an integrated system with multiple stages, a spray tower may be used (e.g., per FIG. 10.1 in Treybal). In addition, conventional tray columns using disk and donut baffles find use (FIGS. 10.4a and 10.4b in Treybal). Further, a column with random packing and flow distributor regions, using packing such as raschig rings, PALL Rings, INTALOX saddles, or berl saddles, find use. In addition, a Podbielniak extractor could optionally be used (FIG. 10.12 in Treybal). Such devices are also described, e.g., in Perry's Chemical Engineering Handbook (Chapter 15, 8th edition, 2008). Columns that find use in the present extraction methods include static extraction columns, agitated extraction columns, mixer-settlers, or centrifugal extractors. Any one of these configurations can be configured to implement the desired number of stages. Economics, as constrained by throughput and equipment space constraints, would define the preferred configuration. An illustrative multistage centrifugal extractor is available from Robatel, Inc. (on the internet at rousselet-robatel.com/products/multistage-centrif-extractors-lx.php). Use of centrifugal countercurrent columns for continuous LLE is also described, e.g., on the internet at cheresources.com/centcontactor.shtml.

According to an embodiment, the majority of the bioproduct is extracted. According to an embodiment, extraction yield, as calculated by dividing the amount of a bioproduct in the extract by the amount of that bioproduct in the fermentation broth, is at least 50%, at least 60%, at least 70%, at least 80%, at least 90%, at least 95%, at least 98%, or at least 99%.

According to an embodiment, the concentration of said bioproduct in said fermentation broth is in the range between 1 g/L and 150 g/L, said extracting is conducted in a counter-current column comprising 2-20 theoretical stages, extractant to fermentation broth flux ratio is in the range between 0.5 and 5, and at least 80% of the bioproduct in said fermentation broth is extracted, at least 95%, at least 98% or at least 99%.

According to an embodiment, the distribution coefficient of the bioproduct between its aqueous solution and said extractant is at least 0.5, at least 0.7, at least 0.9, at least 1.1, at least 1.3, at least 1.5, at least 1.7, at least 2.0, at least 2.5, or at least 3.0.

According to an embodiment, said bioproduct is extracted selectively over water, i.e. the ratio between bioproduct distribution coefficient and water distribution coefficient is greater than 1, e.g. at least 1.5, at least 2, at least 2.5, at least 3, at least 3.5, at least 4, at least 5, at least 7 or at least 10.

Said generated extract comprises said olefin, said bioproduct and water. According to an embodiment, the weight ratio between bioproduct and water in said extract is at least about 5 times greater than said ratio in said fermentation broth, at least 10 times, at least 15 times, at least 20 times, at least 25 times, at least 30 times, at least 40 times or at least 50 times. For example, consider a fermentation broth comprising 2 wt % bioproduct, 2 wt % other solutes and 96 wt % water. According to this embodiment, the bioproduct to water ratio in the extract is greater than 5/48.

According to another embodiment the weight ratio between bioproduct and water in said extract is greater than said ratio in a saturated aqueous solution of said bioproduct at the same temperature.

According to an embodiment, said fermentation broth further comprises a second bioproduct and the weight ratio between said bioproduct and said second bioproduct in said extract is at least about 2 times greater than said ratio in said fermentation broth, at least 4 times greater, at least 6 times greater, at least 8 times greater, at least 10 times greater or at least 15 times greater. According to a related embodiment, said second bioproduct is selected from the group consisting of ethanol, isopropanol, acetone and mixtures thereof.

According to an embodiment, said fermentation broth further comprises a second bioproduct and the extracted fraction of said second bioproduct is smaller than the extracted fraction of said bioproduct. According to a related embodiment, said second bioproduct is selected from the group consisting of ethanol, isopropanol, acetone and mixtures thereof.

According to an embodiment, both said fermentation broth and said extract comprise a carbon source, and the weight ratio between said bioproduct and said carbon source in said extract is at least about 10 times greater than said ratio in said fermentation broth, at least 20 times greater, at least 30 times greater, at least 40 times greater, or at least 50 times greater.

According to an embodiment, both said fermentation broth and said extract comprise a nitrogen source, and the weight ratio between said bioproduct and said nitrogen source in said extract is at least about 10 times greater than said ratio in said fermentation broth, at least 20 times greater, at least 30 times greater, at least 40 times greater, or at least 50 times greater.

According to an embodiment, said extracted fermentation broth comprises cell mass. According to an embodiment, the cell mass content of said extracted fermentation broth is in the range between 0.1 g/L and 100 g/L, between 1 g/L and 90 g/L or between 5 g/L and 80 g/L.

According to an embodiment, said bioproduct is selected from the group consisting of carboxylic acids, dicarboxylic acid and fatty acids and the pH of said broth is adjusted prior to extraction or simultaneously with it to under 6, under 5.8, under 5.6, under 5.4, under 5.2 or under about 5.

According to an embodiment, said second bioproduct is selected from the group consisting of ethanol, isopropanol, acetone, a carboxylic acid and their combinations. According to an embodiment, the distribution coefficient for said bioproduct is in the range between 0.3 and 5. According to an embodiment, the distribution coefficient for ethanol is in the range between 0.05 and 0.5. According to an embodiment, the distribution coefficient for acetic acid is in the range between 0.01 and 0.3. According to an embodiment, the weight ratio between said bioproduct and said second bioproduct in said extract is at least about 1.5, at least 2, at least 3, at least 5, at least 7, or at least 10.

According to an embodiment, bioproduct extraction yield is at least 60%, at least 70%, at least 80%, at least 90%, at least 95%, at least 98% or at least 99%. Of course, bioproduct extraction yields depend upon a number of factors, including the nature of the extractant and the bioproduct, extractant to feed ratio and number of extraction steps in a multiple-step operation mode. The methods described herein provide, for example, relatively high extraction efficiencies of bioproducts while avoiding high costs associated with removal or partial removal of certain extractant components that may be present in the raffinate after extracting has been performed.

According to an embodiment, said second bioproduct is selected from ethanol, isopropanol, acetone, a carboxylic acid and their combinations, bioproduct extraction yield is at least 60%, at least 70%, at least 80%, at least 90%, at least 95%, at least 98% or at least 99% and second bioproduct extraction yield of said second bioproduct is less than about 50%, less than 40%, less than 30%, less than 20% or less than 10%. According to an embodiment, the concentration of said second bioproduct in said raffinate is more than about 0.5 g/L, more than 1 g/L, more than 1.5 g/L, more than 2 g/L, or more than 3 g/L.

According to an embodiment, said second bioproduct comprises a carboxylic acid. According to an embodiment said carboxylic acid may be selected from the group consisting of acetic acid, butyric acid and lactic acid. According to an embodiment, the pH of said broth is adjusted prior to extraction or simultaneously with it to above 5, above 5.5, above 6, above 6.5 or above about 7. According to an embodiment, the weight ratio between said bioproduct and said carboxylic acid in said extract is at least about 10, at least 20 or at least 30. According to an embodiment, extraction yield of said carboxylic acid is less than about 10%, less than 8%, less than 6%, less than 4%, less than 2%, or less than 1%. According to an embodiment, the concentration of said carboxylic acid in said raffinate is more than about 0.5 g/L, more than 1 g/L, more than 1.5 g/L, more than 2 g/L, or more than 3 g/L.

Separation of Extractant from Extract and from Raffinate and Extractant Recycling The method of the first aspect may comprise separating said extract from said raffinate; separating at least a fraction of the bioproduct from said extract; and separating at least a fraction of said extractant from said raffinate to form an extractant-depleted raffinate.

Any form of extract separation from the raffinate is suitable. Typically, the extract is of lower specific gravity and could be separated by decantation. In a mixer-settler unit, separation takes place in the settler. In a column contactor, typically the extract exists near the top of the column and the raffinate near its bottom.

According to an embodiment, separating at least a fraction of the bioproduct from said extract comprises separating at least a fraction of said extractant from said extract to form an extractant-depleted bioproduct solution and separated extractant. According to an embodiment, said separation of extractant from said extract comprises evaporation of the extractant, e.g. via pressure reduction and/or temperature elevation. According to an embodiment, at least 90% of the extractant in the extract is separated, at least 95%, at least 98%, at least 99% or at least 99.5%.

Separating extractant from said raffinate forms an extractant-depleted raffinate and separated extractant. According to an embodiment, said separation of extractant from said raffinate comprises evaporation of the extractant, e.g. via pressure reduction and/or temperature elevation. According to an embodiment, at least 90% of the extractant in the raffinate is separated, at least 95%, at least 98%, at least 99% or at least 99.5%.

According to an embodiment, the method further comprises liquefying at least a fraction of the separated extractant and said liquefying is driven by a refrigerant circuit. According to an embodiment, said liquefied extractant is reused in extracting. In one embodiment, the refrigerant used allows the temperature range for the extractant to fluctuate from about 20° C. to about 30° C., where 20° C. is the condensation temperature and 30° C. is the flash-to-vaporization temperature. To drive this temperature difference, a heat pump with conditions that go between 15° C. and 35° C. may be used. Thus, a 5° C. temperature difference may be used to drive both condensation and vaporization. In this temperature range, for example, the refrigerant R-134a finds use. The energetics of using, reusing, and recycling extractant are improved by driving its vaporization and condensation using a heat pump or refrigerant circuit.

According to an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

According to an embodiment, said vaporizing and said condensing are driven by a refrigerant circuit. In other embodiments, the extractant is condensed using vapor recompression. Vapor recompression is simpler and is commonly used in the oil and gas industries. However, implementing vapor recompression requires a compressor of specific design for use with flammable extractant (e.g. butene). Use of a refrigerant circuit has the advantage that it can be implemented with commercial off-the-shelf refrigerant equipment (e.g., refrigerant compressors, expansion valves, heat exchangers).

Refining the Bioproduct

The extractant-depleted bioproduct solution may comprise the majority of the bioproduct from the fermentation broth. According to an embodiment, due to the extractant selectivity, the bioproduct in said extractant-depleted bioproduct solution may be purer and more concentrated than in the fermentation broth.

According to an embodiment, the weight ratio between said bioproduct and water in said extractant-depleted bioproduct solution is at least about 5 times greater than said ratio in said fermentation broth, at least 10 times, at least 15 times, at least 20 times, at least 25 times, at least 30 times, at least 40 times or at least 50 times.

According to an embodiment, the weight ratio between bioproduct and water in said extractant-depleted bioproduct solution is greater than said ratio in a saturated aqueous solution of said bioproduct at the same temperature. According to an embodiment, said extractant-depleted bioproduct solution splits into two phases. One of those phases is enriched with said bioproduct, i.e. has a bioproduct to water weight ratio greater than that in the extractant-depleted bioproduct solution. Typically said bioproduct-enriched phase is lighter than the other, which is bioproduct depleted compared with the extractant-depleted bioproduct solution. Accordingly, those phases are also referred to as "extract light phase" and "extract heavy phase," respectively.

According to an embodiment, the weight ratio between said bioproduct and water in said extract light phase is at least about 10 times greater than said ratio in said fermentation broth, at least 20 times, at least 30 times, at least 40 times, at least 50 times, at least 60 times, at least 70 times, at least 80 times, at least 90 times or at least 100 times greater.

According to an embodiment, said fermentation broth further comprises a second bioproduct, said bioproduct is extracted selectively over said second bioproduct, but the extract also contains said second bioproduct. According to an embodiment, the weight ratio between bioproduct and water in said extractant-depleted bioproduct solution is greater than said ratio in a saturated aqueous solution of said bioproduct at the same temperature and said extractant-depleted bioproduct solution splits into extract light phase and extract heavy phase. According to an embodiment, said second bioproduct distributes between said two phases. According to an embodiment, the second bioproduct distributes favorably into the extract heavy phase, i.e. its concentration in that heavy phase is greater than its concentration in the extract light phase. According to an embodiment the weight ratio between said bioproduct and said second bioproduct in said extract light phase is at least about 4 times greater than said ratio in said fermentation broth, at least 8 times greater, at least 12 times greater, at least 16 times greater, at least 20 times greater or at least 30 times greater.

According to these embodiments, the extractant-depleted bioproduct solution, and even more so, the extract light phase contain the bioproduct at purity and concentration much higher than those in the fermentation broth. According to these embodiments, the extractant-depleted bioproduct solution, the extract light phase or both are suitable for use as such and/or for conversion into downstream products, e.g. via enzymatic or chemical catalysis.

According to an embodiment, the method further comprises refining said extract light phase to further increase the purity and the concentration of said extract light phase. According to an embodiment, said refining comprises, distillation, ion-exchange, crystallization, membrane separation, chromatographic separation, treatment with an absorbent, e.g. activated carbon, and combinations thereof.

According to an embodiment, the method further comprises refining said extract heavy phase, for the recovery of bioproduct therein. According to an embodiment, said extract heavy phase comprises a second bioproduct and the method further comprises refining said extract heavy phase, for the recovery of said second bioproduct. According to an embodiment, said extract heavy phase is combined with said broth prior to extraction or simultaneously with it. According to an embodiment, extraction uses an extraction column, said broth is introduced via a port near the bottom of the column and said extract heavy phase is introduced via a port at a somewhat higher location.

According to an embodiment, said carbon source comprises liquefied corn, and the method further comprising separating at least a fraction of wet solids from said fermentation broth. According to an embodiment, said separating is conducted prior to said extracting. According to an embodiment, the method further comprises mixing said separated wet solids with a fraction of said extract heavy phase to form a mixture and separating bioproduct and optionally a second bioproduct from said mixture, forming thereby separated bioproduct and a bioproduct-depleted residue. According to an embodiment, said bioproduct-depleted residue is of animal feed quality, containing less than 1000 ppm extractant, less than 500 ppm, less than 100 ppm, less than 50 ppm or less than 10 ppm.

The method further comprises contacting the separated wet solids with a fraction of the extractant-depleted raffinate to form a mixture and separating bioproduct from the mixture to form a bioproduct-depleted residue.

According to an embodiment, provided herein is an animal feed composition comprising said bioproduct-depleted residue.

According to an embodiment, bioproduct concentration in said broth is in the range between 1 wt % and 3 wt % and bioproduct concentration in said extractant-depleted bioproduct solution is at least about 15 wt %, at least 20 wt %, at least 25 wt %, at least 30 wt %, at least 35 wt %, at least 40 wt %, at least 45 wt % or at least 50 wt %.

According to an embodiment, said extractant-depleted bioproduct solution splits into two phases, an extract light phase and an extract heavy phase. According to an embodiment, bioproduct concentration in said extract light phase is at least about 45 wt %, at least 50 wt %, at least 55 wt %, at least 60 wt %, at least 65 wt %, at least 70 wt %, at least 75 wt % or at least 80 wt %. According to an embodiment, bioproduct concentration in said extract heavy phase is less than about 20 wt %, less than 15 wt %, less than 12 wt %, less than 10 wt %, less than 8 wt % or less than 7 wt %.

According to an embodiment, said second bioproduct is selected from the group consisting of ethanol, isopropanol, acetone, a carboxylic acid and their combinations. According to an embodiment, said extractant-depleted bioproduct solution splits into two phases and said second bioproduct distributes between the two phases. According to an embodiment, it distributes favorably into the extract heavy phase, i.e. its concentration in that heavy phase is greater than its concentration in the extract light phase. According to an embodiment, the concentration of said second bioproduct in said fermentation broth is in the range between 0.05 and 10 g/L, its concentration in extract light phase is in the range between 0.1 and 50 g/L and/or its concentration in extract heavy phase is in the range between 50 and 400 g/L.

According to an embodiment, said second bioproduct comprises ethanol and acetone and said extract light phase is refined by distillation. According to an embodiment, said distillation forms a refined bioproduct product, an ethanol product and an acetone product. According to an embodiment, the purity of said refined bioproduct product is greater than 98 wt %, greater than 99 wt %, greater than 99.5 wt %, greater than 99.8 wt % or greater than 99.0 wt %.

According to an embodiment, said refined bioproduct product is used as such, e.g. as fuel additive. Additionally or alternatively, said method further comprises converting said bioproduct into a further product. According to an embodiment, said further product is selected from jet fuel and butadiene. According to an embodiment, said converting comprises chemical catalysis. According to an embodiment, said converting comprises dehydration. According to an embodiment, said bioproduct is crotyl alcohol and said further product is butadiene.

Raffinate Recycling

Said separating extractant from said raffinate generates an extractant-depleted raffinate. According to an embodiment, said extractant-depleted raffinate comprises a carbon source and a nitrogen source. According to an embodiment, the concentration of said carbon source in said extractant-depleted raffinate is in a range between 0.1 and 20 g/L. According to an embodiment, the concentration of said nitrogen source in said extractant-depleted raffinate is in a range between 0.1 and 5 g/L. According to an embodiment, it comprises residual bioproduct and optionally one or two second bioproducts.

The method of the first aspect comprises mixing at least a fraction of said extractant-depleted raffinate with a carbon source and a nitrogen source to form said fermentation medium. Differently put, at least a fraction of said extractant-depleted raffinate is recycled to fermentation.

The extractant has high selectivity to the bioproduct over the nutrients components of the fermentation broth, such as the carbon source, the nitrogen source, vitamins and minerals. According to an embodiment, extractant to broth flux ratio is selected so that, while bioproduct extraction yield is high, that of those nutrients is low. According to an embodiment, less than 10% of the nutrients co-extract with the bioproduct, less than 8%, less than 6%, less than 4%, less than 2% or less than 1%. As a result, more than 90% of those nutrients remain in the extractant-depleted raffinate, more than 92%, more than 94%, more than 96%, more than 98% or more than 99%. Recycling at least a fraction of said extractant-depleted raffinate to the fermentation medium leads therefore to major savings.

According to an embodiment, said second bioproduct comprises ethanol and acetone and said extractant-depleted raffinate comprises ethanol at a concentration between 1 and 15 g/L and acetone at a concentration between 0.5 and 10 g/L.

According to an embodiment, said recycled extractant-depleted raffinate comprises residual amounts of said extractant, e.g. less than 1000 ppm extractant, less than 500 ppm, less than 100 ppm or less than 50 ppm. According to an embodiment, at least a fraction of said extractant evaporates during said fermenting. Optionally said extractant removal is facilitated by gaseous coproducts of fermentation, e.g. CO2.

According to an embodiment, a fraction of said extractant-depleted raffinate is purged prior to said recycle in order to maintain an acceptable steady state concentration of impurities therein.

According to an embodiment, said carbon source comprises liquefied corn and the method further comprises separating wet solids from said broth prior to said contacting, mixing said separated wet solids with a fraction of said extractant-depleted raffinate to form a mixture and separating bioproduct from said mixture to form a bioproduct-depleted residue.

According to an embodiment, said bioproduct-depleted residue is of animal feed quality, containing less than 1000 ppm extractant, less than 500 ppm, less than 100 ppm, less than 50 ppm or less than 10 ppm. According to an embodiment, provided herein is an animal feed composition comprising said bioproduct-depleted residue.

According to various embodiments, the method of the first aspect is characterized by selecting an extractant and extractant/broth ratio that lead to high bioproduct extraction yields, but low yields on extraction of other components so that these other components remain in the raffinate; by using said raffinate to form the fermentation medium of the next cycle, by the relatively high concentration of fermentation coproduct (carboxylic acid, ethanol and/or acetone) in said fermentation medium; by resulting extractant concentration in the fermentation medium and by efficient fermentation in the medium comprising said coproducts and extractant.

A Second Embodiment

According to a second aspect, provided is a method for producing n-butanol comprising: (i) mixing a carbon source, a nitrogen source and an extractant-depleted raffinate to form a fermentation medium; (ii) fermenting said medium with an n-butanol-producing microorganism to form a fermentation broth comprising n-butanol as a first bioproduct at a concentration of less than about 5 wt % and at least one second bioproduct, selected from the group consisting of acetone, ethanol, isopropanol, and a carboxylic acid; (iii) extracting at least a fraction of said fermentation broth with an extractant comprising an olefin to form an extract and a raffinate, wherein both extract and raffinate comprise said extractant, n-butanol, said second bioproduct, and water; and wherein the boiling point of said olefin at atmospheric pressure is under 10° C.; (iv) separating said extract from said raffinate; (v) separating at least a fraction of the n-butanol from said extract; and (v) separating at least a fraction of said extractant from said raffinate to regenerate the extractant-depleted raffinate.

According to an embodiment, the carbon source is a carbohydrate composition. According to an embodiment, said carbohydrate composition comprises at least one hexose, such as glucose and fructose. Alternatively or additionally, said carbohydrate composition comprises at least one pentose, such as xylose or arabinose. Alternatively or additionally, said carbohydrate composition comprises at least one of disaccharides, tri-saccharides, oligosaccharides and polysaccharides. Examples of carbohydrate compositions containing polysaccharides include starch, cellulose and hemicellulose. Examples of carbohydrate compositions containing disaccharides include sucrose, sugarcane juice and sucrose-containing molasses. Suitable carbohydrate compositions include starchy crops, such as corn and wheat, sugarcane and sugar beet and lignocellulosic material. Suitable compositions also include algae and microalgae. Where desired, the carbohydrate compositions may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation.

According to an embodiment, said carbon source results from processing starch or a starch-comprising composition, e.g. corn kernels or wheat grains. According to an embodiment, said carbon source is liquefied corn. Alternatively or additionally, said carbon source results from processing cellulose or a cellulose-comprising composition.

According to an embodiment, the nitrogen source is selected from complex sources, such as corn steep liquor, yeast extract and stillage from ethanol production and components thereof, defined sources, such as ammonia, ammonium salts and urea and combinations thereof.

The method of the second aspect recycles extractant-depleted raffinate to form the fermentation medium of a next cycle. According to an embodiment, said extractant-depleted raffinate is a dilute aqueous solution, optionally comprising at least one of a carbon source, a nitrogen source, ethanol, acetone, isopropanol, a carboxylic acid, and said extractant. According to an embodiment, said extractant-depleted raffinate comprises at least about 1.0 g/L carbon source, at least 2 g/L or at least 3 g/L. According to an embodiment, said carboxylic acid is selected from the group consisting of acetic acid, butyric acid and lactic acid. According to an embodiment, said extractant-depleted raffinate comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L. According to an embodiment, said extractant-depleted raffinate comprises at least about 10 ppm of said of said extractant, at least 20 ppm or at least 30 ppm. According to another embodiment, it comprises less than about 500 ppm of said extractant, less than 400 ppm or less than 300 ppm.

According to the method of the second aspect, said carbon source, a nitrogen source and extractant-depleted raffinate are mixed to form the fermentation medium. According to an embodiment, said extractant-depleted raffinate is modified prior to said mixing. According to a related embodiment, modifying comprises at least one of vaporizing extractant comprised in it, temperature change, addition or removal of water, addition of another component, pH adjustment and heat treatment. According to an embodiment, said fermentation medium further comprises ethanol, acetone, isopropanol, a carboxylic acid and said extractant. According to an embodiment, said at least one of a carbon source, a nitrogen source, ethanol, acetone, isopropanol, a carboxylic acid and said extractant in said fermentation medium result from said extractant-depleted raffinate.

According to an embodiment, said fermentation medium comprises at least about 10 g/L carbon source, at least 20 g/L or at least 30 g/L. According to another embodiment, it comprises less than about 500 g/L carbon source, less than 400 g/L or less than 300 g/L. According to an embodiment, said extractant-depleted raffinate comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L. According to an embodiment, said fermentation medium comprises at least about 10 ppm of said extractant, at least 20 ppm or at least 30 ppm. According to an embodiment, said fermentation medium comprises at least about 0.1 g/L ethanol, at least 0.2 g/L or at least 0.5 g/L. According to another embodiment, it comprises less than about 50 g/L ethanol, less than 40 g/L or less than 30 g/L. According to an embodiment, said fermentation medium comprises at least about 0.1 g/L acetone, at least 0.2 g/L or at least 0.5 g/L. According to another embodiment, it comprises less than about 50 g/L acetone, less than 40 g/L or less than 30 g/L.

Optionally, at least one of said carbon source, said extractant-depleted raffinate and said nitrogen source is treated prior to mixing, e.g., sterilized. Optionally, the product of mixing is further treated, e.g., combined with additional nutrients.

According to an embodiment, a fraction of the carbon source in the fermentation medium and optionally also part of the nitrogen source is consumed during said fermentation, resulting in the formation of n-butanol and a second bioproduct. According to another embodiment, said fermentation medium also comprises a carboxylic acid and at least a fraction of said carboxylic acid is also assimilated.

According to an embodiment, said fermentation is conducted in a fermentor. According to an embodiment, said fermentation is conducted at a temperature between about 25° C. and about 45° C., or between about 30° C. and about 40° C. According to an embodiment, said fermentation also produces CO2. According to a related embodiment, said fermentation medium also comprises extractant and a fraction of said extractant is removed from the fermentor along with vapors, e.g. CO2.

According to an embodiment, said microorganism is viable in a fermentation broth comprising said extractant at a concentration greater than about 0.01 g/L, greater than 0.02 g/L or greater than 0.05 g/L or butanol at a concentration greater than about 1.0 g/L, greater than 2 g/L or greater than 5 g/L or ethanol at a concentration greater than about 1.0 g/L, greater than 2 g/L or greater than 5 g/L or acetone at a concentration greater than about 1.0 g/L, greater than 2 g/L or greater than 5 g/L or combinations thereof.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of n-butanol production, e.g., including without limitation microorganisms of the phylum Firmicutes, e.g., including without limitation Clostridia. Illustrative Clostridia include, e.g., *Clostridium* and *Eubacterium*. Illustrative members of the genus *Clostridium* include without limitation, *Clostridium butyricum, Clostridium acetobutylicum, Clostridium saccharoperbutylacetonicum, Clostridium saccharobutylicum, Clostridium beijerickii, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum*, and *Clostridium autoethanogenum*. Illustrative *Eubacterium* include *Eubacterium limosum*.

Suitable bacteria and fungi also include those that are capable of hydrolyzing carbon sources and can be genetically engineered to produce n-butanol. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus, Saccharomycopsis, Aspergillus, Pichia, Schwanniomyces* and *Polysporus*. The fungi may be able to perform the conversion aerobically or anaerobically. Examples of anaerobic fungi include, without limitation, *Piromyces* species (e.g., strain E2), *Orpinomyces* species (e.g. *Orpinomyces bovis*), *Neocallimastix* species (*N. frontalis*), *Caecomyce* species, *Anaeromyces* species and *Ruminomyces* species.

According to other embodiments, the microorganism is a temperature resistant microorganism. In other embodiments, the microorganism is an extractant resistant microorganism.

According to the method of the second aspect said fermentation forms a fermentation broth comprising n-butanol. According to an embodiment, the concentration of n-butanol in said fermentation broth is less than about 5 wt %, less than 4 wt %, less than 3 wt % or less than 2 wt %. According to an embodiment, the concentration of n-butanol in said fermentation broth is in the range between about 0.5 wt % and about 5 wt % or between about 1 wt % and about 3 wt %.

According to some embodiments, the microorganism has a productivity of at least about 0.5 g/L per hour of n-butanol in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour.

According to an embodiment, said second bioproduct is selected from the group consisting of ethanol, isopropanol, acetone, a carboxylic acid and their combinations.

The method of the second aspect comprises extracting at least a fraction of said fermentation broth with an extractant comprising an olefin to form an extract and a raffinate, wherein both extract and raffinate comprise said extractant, n-butanol, second bioproduct, and water; and wherein the boiling point of said olefin at atmospheric pressure is under 10° C. According to an embodiment, said extracting is conducted at a temperature greater than 10° C. According to an embodiment, said extracting is conducted at super-atmospheric pressure.

According to an embodiment, said olefin is selected from the group consisting of 1-butene, 2-butene and iso-butene.

According to an embodiment, said extracted fermentation broth comprises cell mass. According to this embodiment, cell mass is present in the fermentation broth during extraction.

According to an embodiment, said extractant comprises at least 70 wt %, 75 wt %, 80 wt %, 85 wt %, 90 wt % or at least 95 wt % olefin. According to an embodiment, said extractant further comprises at least one of dimethyl ether, methyl-ethyl ether, and diethyl ether.

According to an embodiment, said extracting is conducted at a temperature between about 20° C. and about 50° C., between about 25° C. and about 45° C. or between about 30° C. and about 40° C. In various embodiments, extracting is conducted at about fermentation temperature. According to an embodiment, extraction is conducted in an extraction column and the temperature changes along the column.

In various embodiments, extracting is conducted at pressure between about 1.5 bar and about 10 bar, between about 2 bar and about 9 bar or between about 3 bar and about 8 bar.

According to an embodiment, extracting comprises mixing said fermentation broth with said extractant, followed by separating the generated extractant-rich phase (extract, typically the lighter phase) from the generated water-rich phase (raffinate, typically the heavier phase). Any form of mixing is suitable. Any form of phase separation is suitable. According to an embodiment, said extracting comprises multiple steps, e.g. between 2 and 30 stages, between 2 and 20 stages or between 2 and 10 stages. According to an embodiment, extracting is conducted in a counter-current mode. According to an embodiment, extracting is conducted in a series of mixer settlers, in an extraction column or in a centrifugal contactor.

According to varying embodiments, the flux ratio of extractant to broth is in the range of from about 0.2 to about 20, from about 0.3 to about 10, from about 0.4 to about 8 or from about 0.5 to about 3.

According to an embodiment, the majority of the n-butanol is extracted. According to an embodiment, extraction yield, as calculated by dividing the amount of n-butanol in the extract by the amounts of n-butanol in the fermentation broth, is at least 50%, at least 60%, at least 70%, at least 80%, at least 90%, at least 95%, at least 98%, or at least 99%.

According to an embodiment, the concentration of n-butanol in said fermentation broth is in the range between 1 g/L and 100 g/L, said extracting is conducted in a counter-current mode comprising 2-20 theoretical stages, extractant to fermentation broth flux ratio is in the range between 0.5 and 5, and at least 80% of the n-butanol in said fermentation broth is extracted, at least 95%, at least 98%, or at least 99%.

According to an embodiment, the distribution coefficient of n-butanol between its aqueous solution and said extractant is at least 0.5, at least 0.7, at least 0.9, at least 1.1, at least 1.3, at least 1.5, at least 1.7, at least 2.0, at least 2.5, at least 3.0, at least 3.5 or at least 4.0.

According to an embodiment, n-butanol is extracted selectively over water, i.e. the ratio between n-butanol distribution coefficient and water distribution coefficient is greater than 1, e.g. at least 1.5, at least 2, at least 2.5, at least 3, at least 3.5, at least 4, at least 5, at least 7 or at least 10.

Said generated extract may comprise said extractant, n-butanol and water. According to an embodiment, the weight ratio between n-butanol and water in said extract is at least about 5 times greater than said ratio in said fermentation broth, at least 10 times, at least 15 times, at least 20 times, at least 25 times, at least 30 times, at least 40 times or at least 50 times greater. For example, consider a fermentation broth comprising 2% n-butanol, 2% other solutes and 96% water. According to this embodiment, the n-butanol to water ratio in the extract is greater than $5/48$.

According to another embodiment the weight ratio between n-butanol and water in said extract is greater than said ratio in a saturated aqueous solution of n-butanol at the same temperature. For example, at 25° C., saturated aqueous solution contains about 7.3 wt % n-butanol, i.e. n-butanol/water weight ratio of about 0.079. According to this embodiment, that weight ratio in the extract is greater than 0.079, e.g. greater than 0.1, greater than 0.2, greater than 0.3, greater than 0.4 or greater than 0.5.

According to an embodiment, the weight ratio between n-butanol and said second bioproduct in said extract is at least about 2 times greater than said ratio in said fermentation broth, at least 4 times greater, at least 6 times greater, at least 8 times greater, at least 10 times greater or at least 15 times greater. According to a related embodiment, said second bioproduct is selected from the group consisting of ethanol, isopropanol, acetone and mixtures thereof.

According to an embodiment, the extracted fraction of said second bioproduct is smaller than the extracted fraction of n-butanol. According to a related embodiment, said second bioproduct is selected from the group consisting of ethanol, isopropanol, acetone and mixtures thereof.

According to an embodiment, both said fermentation broth and said extract comprise a carbon source, and the weight ratio between n-butanol and said carbon source in said extract is at least about 10 times greater than said ratio in said fermentation broth, at least 20 times greater, at least 30 times greater, at least 40 times greater, or at least 50 times greater.

According to an embodiment, both said fermentation broth and said extract comprise a nitrogen source, and the weight ratio between n-butanol and said nitrogen source in said extract is at least about 10 times greater than said ratio in said fermentation broth, at least 20 times greater, at least 30 times greater, at least 40 times greater, or at least 50 times greater.

According to an embodiment, said extracted fermentation broth comprises cell mass. According to an embodiment, the cell mass content of said extracted fermentation broth is in the range between 0.1 g/L and 100 g/L, between 1 g/L and 90 g/L or between 5 g/L and 80 g/L.

According to an embodiment, said second bioproduct is selected from ethanol, isopropanol, acetone, a carboxylic acid and their combinations. According to an embodiment, the distribution coefficient for n-butanol is in the range between 0.3 and 5. According to an embodiment, the distribution coefficient for ethanol is in the range between 0.05 and 0.5. According to an embodiment, the distribution coefficient for acetic acid is in the range between 0.01 and 0.3. According to an embodiment, the weight ratio between n-butanol and said second bioproduct in said extract is at least about 1.5, at least 2, at least 3, at least 5, at least 7, or at least 10.

According to an embodiment, n-butanol extraction yield is at least 60%, at least 70%, at least 80%, at least 90%, at least 95%, at least 98%, or at least 99%.

According to an embodiment, said second bioproduct is selected from the group consisting of ethanol, isopropanol, acetone, a carboxylic acid and their combinations, n-butanol extraction yield is at least 60%, at least 70%, at least 80%, at least 90%, at least 95%, at least 98% or at least 99% and second bioproduct extraction yield is less than 50%, less than 40%, less than 30%, less than 20% or less than 10%. According to an embodiment, the concentration of said second bioproduct in said raffinate is more than about 0.5 g/L, more than 1 g/L, more than 1.5 g/L, more than 2 g/L, or more than 3 g/L.

According to an embodiment, said second bioproduct comprises a carboxylic acid. According to an embodiment said carboxylic acid is selected from the group consisting of acetic acid, butyric acid, lactic acid and combinations thereof. According to an embodiment, the pH of said broth is adjusted prior to extraction or simultaneously with it to above 5, above 5.5, above 6, above 6.5 or above about 7. According to an embodiment, the weight ratio between n-butanol and said carboxylic acid in said extract is at least 10, at least 20 or at least 30. According to an embodiment, extraction yield of said carboxylic acid is less than about 10%, less than 8%, less than 6%, less than 4%, less than 2%, or less than 1%. According to an embodiment, the concentration of said carboxylic acid in said raffinate is more than about 0.5 g/L, more than 1 g/L, more than 1.5 g/L, more than 2 g/L, or more than 3 g/L.

The method of the second aspect may comprise separating said extract from said raffinate, separating at least a fraction of n-butanol from said extract, and separating at least a fraction of said extractant from said raffinate to form an extractant-depleted raffinate.

Any form of extract separation from the raffinate is suitable. Typically, the extract is of lower specific gravity and could be separated by decantation. In a mixer-settler unit, separation takes place in the settler. In a column contactor, typically the extract exists near the top of the column and the raffinate near its bottom.

According to an embodiment, separating at least a fraction of n-butanol from said extract comprises separating at least a fraction of said extractant from said extract to form an extractant-depleted n-butanol solution and separated extractant. According to an embodiment, said separation of extractant from said extract comprises evaporation of the extractant, e.g. via pressure reduction and/or temperature elevation. According to an embodiment, at least 90% of the extractant in the extract is separated, at least 95%, at least 98%, at least 99% or at least 99.5%.

Separating extractant from said raffinate forms an extractant-depleted raffinate and separated extractant. According to an embodiment, said separation of extractant from said raffinate comprises evaporation of the extractant, e.g. via pressure reduction and/or temperature elevation. According to an embodiment, at least 90% of the extractant in the raffinate is separated, at least 95%, at least 98%, at least 99% or at least 99.5%.

According to an embodiment, the method further comprises liquefying at least a fraction of the separated extractant and said liquefying is driven by a refrigerant circuit. According to an embodiment, said liquefied extractant is reused in extracting.

According to an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

N-Butanol Refining

The extractant-depleted n-butanol solution may comprise the majority of n-butanol from the fermentation broth. According to an embodiment, due to the extractant selectivity, n-butanol in said extractant-depleted n-butanol solution is purer and more concentrated than in the fermentation broth.

According to an embodiment, the weight ratio between n-butanol and water in said extractant-depleted n-butanol solution is at least about 5 times greater than said ratio in said fermentation broth, at least 10 times, at least 15 times, at least 20 times, at least 25 times, at least 30 times, at least 40 times or at least 50 times greater.

According to an embodiment, the weight ratio between n-butanol and water in said extractant-depleted n-butanol solution is greater than said ratio in a saturated aqueous solution of n-butanol at the same temperature. According to an embodiment, said extractant-depleted n-butanol solution splits into two phases. One of those phases is enriched with n-butanol, i.e. has an n-butanol to water weight ratio greater than that in the extractant-depleted n-butanol solution. Said n-butanol-enriched phase is lighter than the other, which is n-butanol depleted compared with the extractant-depleted n-butanol solution. Accordingly, those phases are also referred to as "extract light phase" and "extract heavy phase," respectively.

According to an embodiment, the weight ratio between n-butanol and water in said extract light phase is at least about 10 times greater than said ratio in said fermentation broth, at least 20 times, at least 30 times, at least 40 times, at least 50 times, at least 60 times, at least 70 times, at least 80 times, at least 90 times, or at least 100 times greater.

According to an embodiment, n-butanol is extracted selectively over said second bioproduct, but the extract also contains said second bioproduct. According to an embodiment, the weight ratio between n-butanol and water in said extractant-depleted n-butanol solution is greater than said ratio in a saturated aqueous solution of n-butanol at the same temperature and said extractant-depleted n-butanol solution splits into extract light phase and extract heavy phase. According to an embodiment, said second bioproduct distributes between said two phases. According to an embodiment, it distributes favorably into the extract heavy phase, i.e. its concentration in that heavy phase is greater than its concentration in the extract light phase. According to an embodiment the weight ratio between n-butanol and said second bioproduct in said extract light phase is at least about 4 times greater than said ratio in said fermentation broth, at least 8 times greater, at least 12 times greater, at least 16 times greater, at least 20 times greater, or at least 30 times greater.

According to these embodiments, the extractant-depleted n-butanol solution, and even more so, the extract light phase contain n-butanol at purity and concentration much higher than those in the fermentation broth. According to these embodiments, the extractant-depleted n-butanol solution, the extract light phase or both are suitable for use as such and/or for conversion into downstream products, e.g. via enzymatic or chemical catalysis.

According to an embodiment, the method further comprises refining said extract light phase to further increase the purity and n-butanol concentration of said extract light phase. According to an embodiment, said refining comprises, at least one of distillation, ion-exchange, crystallization, membrane separation, chromatographic separation, treatment with an absorbent, e.g. activated carbon, and combinations thereof.

According to an embodiment, the method further comprises refining said extract heavy phase, for the recovery of n-butanol therein. According to an embodiment, the method further comprises refining said extract heavy phase, for the recovery of said second bioproduct. According to an embodiment, said extract heavy phase is combined with said broth prior to extraction or simultaneously with it. According to an embodiment, extraction uses an extraction column, said broth is introduced via a port near the bottom of the column and said extract heavy phase is introduced via a port at a somewhat higher location.

According to an embodiment, n-butanol concentration in said broth is in the range between 1 wt % and 3 wt % and n-butanol concentration in said extractant-depleted n-butanol solution is at least about 15 wt %, at least 20 wt %, at least 25 wt %, at least 30 wt %, at least 35 wt %, at least 40 wt %, at least 45 wt % or at least 50 wt %.

According to an embodiment, said extractant-depleted n-butanol solution splits into two phases, an extract light phase and an extract heavy phase. According to an embodiment, n-butanol concentration in said extract light phase is at least about 45 wt %, at least 50 wt %, at least 55 wt %, at least 60 wt %, at least 65 wt %, at least 70 wt %, at least 75 wt % or at least 80 wt %. According to an embodiment, n-butanol concentration in said extract heavy phase is less than about 20 wt %, less than 15 wt %, less than 12 wt %, less than 10 wt %, less than 8 wt % or less than 7 wt %.

According to an embodiment, said second bioproduct is selected from the group consisting of ethanol, isopropanol, acetone, a carboxylic acid and their combinations. According to an embodiment, said extractant-depleted n-butanol solution splits into two phases and said second bioproduct distributes between the two phases. According to an embodiment, it distributes favorably into the extract heavy phase, i.e. its concentration in that heavy phase is greater than its concentration in the extract light phase. According to an embodiment, the concentration of said second bioproduct in said fermentation broth is in the range between 0.05 and 10 g/L, its concentration in the extract light phase is in the range between 0.1 and 50 g/L and/or its concentration in the extract heavy phase is in the range between 50 and 400 g/L.

According to an embodiment, said second bioproduct comprises ethanol and acetone and said extract light phase is refined by distillation. According to an embodiment, said distillation forms a refined n-butanol product, an ethanol product and an acetone product. According to an embodiment, said the purity of said refined n-butanol product is greater than 98 wt %, greater than 99 wt %, greater than 99.5 wt %, greater than 99.8 wt %, or greater than 99.0 wt %.

According to an embodiment, said refined n-butanol product is used as such, e.g. as fuel additive. Additionally or alternatively, said method further comprises converting said n-butanol into a further product. According to an embodiment, said further product is selected from jet fuel and butadiene. According to an embodiment, said converting comprises chemical catalysis. According to an embodiment, said converting comprises dehydration.

Raffinate Recycling

Said separating extractant from said raffinate generates an extractant-depleted raffinate. According to an embodiment, said extractant-depleted raffinate comprises a carbon source and a nitrogen source. According to an embodiment, the concentration of said carbon source in said extractant-depleted raffinate is in a range between 0.1 and 20 g/L. According to an embodiment, the concentration of said nitrogen source in said extractant-depleted raffinate is in a range between 0.1 and 5 g/L. According to an embodiment, it comprises residual n-butanol and optionally at least one second bioproducts.

The method of the second aspect comprises mixing at least a fraction of said extractant-depleted raffinate with a carbon source and a nitrogen source to form said fermentation medium. Differently put, at least a fraction of said extractant-depleted raffinate is recycled to fermentation.

The extractant has high selectivity to n-butanol over the nutrients components of the fermentation broth, such as the carbon source, the nitrogen source, vitamins and minerals. According to an embodiment, extractant to broth flux ratio is selected so that, while n-butanol extraction yield is high, that of those nutrients is low. According to an embodiment, less than 10% of the nutrients co-extract with n-butanol, less than 8%, less than 6%, less than 4%, less than 2% or less than 1%. As a result, more than 90% of those nutrients remain in the extractant-depleted raffinate, more than 92%, more than 94%, more than 96%, more than 98% or more than 99%. Recycling at least a fraction of said extractant-depleted raffinate to the fermentation medium leads therefore to major savings.

According to an embodiment, said extractant-depleted raffinate comprises ethanol at a concentration between 1 and 15 g/L and acetone at a concentration between 0.5 and 10 g/L. According to an embodiment, the concentration of ethanol and acetone in the fermentation broth is greater than that in the extractant-depleted raffinate.

According to an embodiment, said recycled extractant-depleted raffinate comprises residual amounts of said extractant, e.g. less than 1000 ppm extractant, less than 500 ppm, less than 100 ppm or less than 50 ppm. According to an embodiment, at least a fraction of said extractant evaporates during said fermenting. Optionally said extractant removal is facilitated by gaseous coproducts of fermentation, e.g. $CO_2$.

According to an embodiment, a fraction of said extractant-depleted raffinate is purged prior to said recycling in order to maintain an acceptable steady state concentration of impurities therein.

According to various embodiments, the method of the second aspect is characterized by selecting an extractant and extractant/broth ratio that lead to high butanol extraction yields, but low yields on extraction of other components so that these other components remain in the raffinate; by using said raffinate to form the fermentation medium of the next cycle, by the relatively high concentration of fermentation coproduct (carboxylic acid, ethanol and/or acetone) in said fermentation medium; by resulting extractant concentration in the fermentation medium and by efficient fermentation in the medium comprising said coproducts and extractant.

A Third Embodiment

According to a third aspect, provided is a method for producing crotyl alcohol comprising: (i) mixing a carbon source, a nitrogen source, and extractant-depleted raffinate to form fermentation medium; (ii) fermenting said medium with a crotyl alcohol-producing microorganism to form a fermentation broth comprising crotyl alcohol at a concentration of less than about 5% and at least one second bioproduct, selected from the group consisting of acetone, ethanol, isopropanol, and a carboxylic acid; (iii) extracting at least a fraction of said fermentation broth with an extractant comprising an olefin to form an extract and a raffinate, wherein both extract and raffinate comprise said extractant, crotyl alcohol, said second bioproduct, and water; and wherein the boiling point of said olefin at atmospheric pressure is under 10° C.; (iv) separating said extract from said raffinate; (v) separating at least a fraction of the crotyl alcohol from said extract; and (v) separating at least a fraction of said extractant from said raffinate to regenerate the extractant-depleted raffinate.

According to an embodiment, the carbon source is a carbohydrate composition. According to an embodiment, said carbohydrate composition comprises at least one hexose, such as glucose and fructose. Alternatively or additionally, said carbohydrate composition comprises at least one pentose, such as xylose or arabinose. Alternatively or additionally, said carbohydrate composition comprises at least one of disaccharides, tri-saccharides, oligosaccharides and polysaccharides. Examples of carbohydrate compositions containing polysaccharides include starch, cellulose and hemicellulose. Examples of carbohydrate compositions containing disaccharides include sucrose, sugarcane juice and sucrose-containing molasses. Suitable carbohydrate compositions include starchy crops, such as corn and wheat, sugarcane and sugar beet and lignocellulosic material. Suitable compositions also include algae and microalgae. Where desired, the carbohydrate compositions may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation.

According to an embodiment, said carbon source results from processing starch or a starch-comprising composition, e.g. corn kernels or wheat grains. According to an embodiment, said carbon source is liquefied corn. Alternatively or additionally, said carbon source results from processing cellulose or a cellulose-comprising composition.

According to an embodiment, the nitrogen source is selected from complex sources, such as corn steep liquor, yeast extract and stillage from ethanol production and components thereof, defined sources, such as ammonia, ammonium salts and urea and combinations thereof.

The method of the third aspect may recycle extractant-depleted raffinate to form the fermentation medium of a next cycle. According to an embodiment, said extractant-depleted raffinate is a dilute aqueous solution, optionally comprising at least one of a carbon source, a nitrogen source, ethanol, acetone, isopropanol, a carboxylic acid and said extractant. According to an embodiment, said extractant-depleted raffinate comprises at least about 1.0 g/L carbon source, at least 2 g/L or at least 3 g/L. According to an embodiment, said carboxylic acid is selected from the group consisting of acetic acid, butyric acid and lactic acid. According to an embodiment, said extractant-depleted raffinate comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L. According to an embodiment, said extractant-depleted raffinate comprises at least about 10 ppm of said of said extractant, at least 20 ppm or at least 30 ppm. According to another embodiment, it comprises less than about 500 ppm of said extractant, less than 400 ppm or less than 300 ppm.

According to the method of the third aspect, said carbon source, a nitrogen source and extractant-depleted raffinate are mixed to form the fermentation medium. According to an embodiment, said extractant-depleted raffinate is modified prior to said mixing. According to a related embodiment, modifying comprises at least one of vaporizing extractant comprised in it, temperature change, addition or removal of water, addition of another component, pH adjustment and heat treatment. According to an embodiment, said fermentation medium further comprises at least one of a carbon source, a nitrogen source, ethanol, acetone, isopropanol, a carboxylic acid and said extractant. According to an embodiment, said at least one of a carbon source, a nitrogen source, ethanol, acetone, isopropanol, a carboxylic acid and said extractant in said fermentation medium result from said extractant-depleted raffinate.

According to an embodiment, said fermentation medium comprises at least about 10 g/L carbon source, at least 20 g/L or at least 30 g/L. According to another embodiment, it comprises less than about 500 g/L carbon source, less than 400 g/L or less than 300 g/L. According to an embodiment, said extractant-depleted raffinate comprises at least about 0.1 g/L carboxylic acid, at least 0.2 g/L or at least 0.5 g/L. According to another embodiment, it comprises less than about 50 g/L carboxylic acid, less than 40 g/L or less than 30 g/L. According to an embodiment, said fermentation medium comprises at least about 10 ppm of said extractant, at least 20 ppm or at least 30 ppm. According to an embodiment, said fermentation medium comprises at least about 0.1 g/L ethanol, at least 0.2 g/L or at least 0.5 g/L. According to another embodiment, it comprises less than about 50 g/L ethanol, less than 40 g/L or less than 30 g/L. According to an embodiment, said fermentation medium comprises at least about 0.1 g/L acetone, at least 0.2 g/L or at least 0.5 g/L. According to another embodiment, it comprises less than about 50 g/L acetone, less than 40 g/L or less than 30 g/L.

Optionally, at least one of said carbon source, said extractant-depleted raffinate and said nitrogen source is treated prior to mixing, e.g., sterilized. Optionally, the product of mixing is further treated, e.g., combined with additional nutrients.

According to an embodiment, a fraction of the carbon source in the fermentation medium and optionally also part of the nitrogen source is consumed during said fermentation, resulting in the formation of crotyl alcohol and a second bioproduct. According to another embodiment, said fermentation medium also comprises a carboxylic acid and at least a fraction of said carboxylic acid is also assimilated.

According to an embodiment, said fermentation is conducted in a fermentor. According to an embodiment, said fermentation is conducted at a temperature between about 25° C. and about 45° C., or between about 30° C. and about 40° C. According to an embodiment, said fermentation also produces CO2. According to a related embodiment, said fermentation medium also comprises extractant and a fraction of said extractant is removed from the fermentor along with vapors, e.g. CO2.

According to an embodiment, said microorganism is viable in a fermentation broth comprising said extractant at a concentration greater than about 0.01 g/L, greater than 0.02 g/L or greater than 0.05 g/L or crotyl alcohol at a concentration greater than about 1.0 g/L greater than 2 g/L or greater than 5 g/L or ethanol at a concentration greater than about 1.0 g/L, greater than 2 g/L or greater than 5 g/L or acetone at a concentration greater than about 1.0 g/L, greater than 2 g/L or greater than 5 g/L or combinations thereof.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of crotyl alcohol production, e.g., including without limitation microorganisms of the phylum Firmicutes, e.g., including without limitation Clostridia. Illustrative Clostridia include, e.g., *Clostridium* and *Eubacterium*. Illustrative members of the genus *Clostridium* include without limitation, *Clostridium butyricum*, *Clostridium acetobutylicum*, *Clostridium saccharoperbutylacetonicum*, *Clostridium saccharobutylicum*, *Clostridium beijerickii*, *Clostridium pasteurianum*, *Clostridium kluyveri*, *Clostridium carboxidovorans*, *Clostridium phytofermentens*, *Clostridium thermocellum*, *Clostridium cellulolyticum*, *Clostridium cellulovorans*, *Clostridium clariflavum*, *Clostridium ljungdahlii*, *Clostridium acidurici*, *Clostridium tyrobutyricum*, and *Clostridium autoethanogenum*. Illustrative *Eubacterium* include *Eubacterium limosum*.

Suitable bacteria and fungi also include those that are capable of hydrolyzing carbon sources and can be genetically engineered to produce crotyl alcohol. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus*, *Saccharomycopsis*, *Aspergillus*, *Pichia*, *Schwanniomyces*, and *Polysporus*.

The fungi may be able to perform the conversion aerobically or anaerobically. Examples of anaerobic fungi include, without limitation, *Piromyces* species (e.g., strain E2), *Orpinomyces* species (e.g. *Orpinomyces bovis*), *Neocallimastix* species (*N. frontalis*), *Caecomyce* species, *Anaeromyces* species and *Ruminomyces* species.

According to other embodiments, the microorganism is a temperature resistant microorganism. In other embodiments, the microorganism is an extractant resistant microorganism.

According to the method of the third aspect said fermentation forms a fermentation broth comprising crotyl alcohol. According to an embodiment, the concentration of crotyl alcohol in said fermentation broth is less than about 5 wt %, less than 4 wt %, less than 3 wt %, or less than 2 wt %. According to an embodiment, the concentration of crotyl alcohol in said fermentation broth is in the range between about 0.5 wt % and about 5 wt % or between about 1 wt % and about 3 wt %.

According to some embodiments, the microorganism has a productivity of at least about 0.5 g/L per hour of crotyl alcohol in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour.

According to an embodiment, said second bioproduct is selected from the group consisting of ethanol, isopropanol, acetone, a carboxylic acid and their combinations.

The method of the third aspect comprises extracting at least a fraction of said fermentation broth with an extractant comprising an olefin to form an extract and a raffinate, wherein both extract and raffinate comprise said extractant, crotyl alcohol, second bioproduct, and water; and wherein the boiling point of said olefin at atmospheric pressure is under 10° C. According to an embodiment, said extracting is conducted at a temperature greater than 10° C. According to an embodiment, said extracting is conducted at super-atmospheric pressure.

According to an embodiment, said olefin is selected from the group consisting of 1-butene, 2-butene and iso-butene.

According to an embodiment, said extracted fermentation broth comprises cell mass. According to this embodiment, cell mass is present in the fermentation broth during extraction.

According to an embodiment, said extractant comprises at least 70%, 75%, 80%, 85%, 90%, or at least 95% olefin. According to an embodiment, said extractant further comprises at least one of dimethyl ether, methyl-ethyl ether, and diethyl ether.

According to an embodiment, said extracting is conducted at a temperature between about 20° C. and about 50° C., between about 25° C. and about 45° C. or between about 30° C. and about 40° C. In various embodiments, extracting is conducted at about fermentation temperature. According to an embodiment, extraction is conducted in an extraction column and the temperature changes along the column.

In various embodiments, extracting is conducted at pressure between about 1.5 bar and about 10 bar, between about 2 bar and about 9 bar or between about 3 bar and about 8 bar.

According to an embodiment, extracting comprises mixing said fermentation broth with said extractant, followed by separating the generated extractant-rich phase (extract, typically the lighter phase) from the generated water-rich phase (raffinate, typically the heavier phase). Any form of mixing is suitable. Any form of phase separation is suitable. According to an embodiment, said extracting comprises multiple steps, e.g. between 2 and 30 stages, between 2 and 20 stages or between 2 and 10 stages. According to an embodiment, extracting is conducted in a counter-current mode. According to an embodiment, extracting is conducted in a series of mixer settlers, in an extraction column or in a centrifugal contactor.

According to varying embodiments, the flux ratio of extractant to broth is in the range of from about 0.2 to about 20, from about 0.3 to about 10, from about 0.4 to about 8 or from about 0.5 to about 3.

According to an embodiment, the majority of the crotyl alcohol is extracted. According to an embodiment, extraction yield, as calculated by dividing the amount of crotyl alcohol in the extract by the amounts of crotyl alcohol in the fermentation broth, is at least 50%, at least 60%, at least 70%, at least 80%, at least 90%, at least 95%, at least 98%, or at least 99%.

According to an embodiment, the concentration of crotyl alcohol in said fermentation broth is in the range between 1 g/L and 100 g/L, said extracting is conducted in a counter-current mode comprising 2-20 theoretical stages, extractant to fermentation broth flux ratio is in the range between 0.5 and 5, and at least 80% of the crotyl alcohol in said fermentation broth is extracted, at least 95%, at least 98% or at least 99%.

According to an embodiment, the distribution coefficient of crotyl alcohol between its aqueous solution and said extractant is at least 0.5, at least 0.7, at least 0.9, at least 1.1, at least 1.3, at least 1.5, at least 1.7, at least 2.0, at least 2.5, at least 3.0, at least 3.5 or at least 4.0.

According to an embodiment, crotyl alcohol is extracted selectively over water, i.e. the ratio between crotyl alcohol distribution coefficient and water distribution coefficient is greater than 1, e.g. at least 1.5, at least 2, at least 2.5, at least 3, at least 3.5, at least 4, at least 5, at least 7, or at least 10.

Said generated extract comprises said extractant, crotyl alcohol and water. According to an embodiment, the weight ratio between crotyl alcohol and water in said extract is at least about 5 times greater than said ratio in said fermentation broth, at least 10 times, at least 15 times, at least 20 times, at least 25 times, at least 30 times, at least 40 times or at least 50 times greater. For example, consider a fermentation broth comprising 2% crotyl alcohol, 2% other solutes and 96% water. According to this embodiment, the crotyl alcohol to water ratio in the extract is greater than 5/48.

According to another embodiment the weight ratio between crotyl alcohol and water in said extract is greater than said ratio in a saturated aqueous solution of crotyl alcohol at the same temperature, e.g. greater than 0.1, greater than 0.2, greater than 0.3, greater than 0.4 or greater than 0.5.

According to an embodiment, the weight ratio between crotyl alcohol and said second bioproduct in said extract is at least about 2 times greater than said ratio in said fermentation broth, at least 4 times greater, at least 6 times greater, at least 8 times greater, at least 10 times greater or at least 15 times greater. According to a related embodiment, said second bioproduct is selected from the group consisting of ethanol, isopropanol, acetone and mixtures thereof.

According to an embodiment, the extracted fraction of said second bioproduct is smaller than the extracted fraction of crotyl alcohol. According to a related embodiment, said second bioproduct is selected from the group consisting of ethanol, isopropanol, acetone and mixtures thereof.

According to an embodiment, both said fermentation broth and said extract comprise a carbon source, and the weight ratio between crotyl alcohol and said carbon source in said extract is at least about 10 times greater than said ratio in said fermentation broth, at least 20 times greater, at least 30 times greater, at least 40 times greater, or at least 50 times greater.

According to an embodiment, both said fermentation broth and said extract comprise a nitrogen source, and the weight ratio between crotyl alcohol and said nitrogen source in said extract is at least about 10 times greater than said ratio in said fermentation broth, at least 20 times greater, at least 30 times greater, at least 40 times greater, or at least 50 times greater.

According to an embodiment, said extracted fermentation broth comprises cell mass. According to an embodiment, the cell mass content of said extracted fermentation broth is in the range between 0.1 g/L and 100 g/L, between 1 g/L and 90 g/L or between 5 g/L and 80 g/L.

According to an embodiment, said second bioproduct is selected from ethanol, isopropanol, acetone, a carboxylic acid and their combinations. According to an embodiment, the distribution coefficient for crotyl alcohol is in the range between 0.3 and 5. According to an embodiment, the distribution coefficient for ethanol is in the range between 0.05 and 0.5. According to an embodiment, the distribution coefficient for acetic acid is in the range between 0.01 and 0.3. According to an embodiment, the weight ratio between crotyl alcohol and said second bioproduct in said extract is at least 1.5, at least 2, at least 3, at least 5, at least 7, or at least 10.

According to an embodiment, crotyl alcohol extraction yield is at least 60%, at least 70%, at least 80%, at least 90%, at least 95%, at least 98% or at least 99%.

According to an embodiment, said second bioproduct is selected from the group consisting of ethanol, isopropanol, acetone, a carboxylic acid and their combinations, crotyl alcohol extraction yield is at least 60%, at least 70%, at least 80%, at least 90%, at least 95%, at least 98% or at least 99% and second bioproduct extraction yield is less than 50%, less than 40%, less than 30%, less than 20% or less than 10%.

According to an embodiment, said second bioproduct comprises a carboxylic acid. According to an embodiment said carboxylic acid is selected from the group consisting of acetic acid, butyric acid, lactic acid and combinations thereof. According to an embodiment, the pH of said broth is adjusted prior to extraction or simultaneously with it to above 5, above 5.5, above 6, above 6.5 or above about 7. According to an embodiment, the weight ratio between crotyl alcohol and said carboxylic acid in said extract is at least 10 at least 20 or at least 30. According to an embodiment, extraction yield of said carboxylic acid is less than about 10%, less than 8%, less than 6%, less than 4%, less than 2%, or less than 1%. According to an embodiment, the concentration of said carboxylic acid in said raffinate is more than about 0.5 g/L, more than 1 g/L, more than 1.5 g/L, more than 2 g/L, or more than 3 g/L.

The method of the third aspect may comprise separating said extract from said raffinate, separating at least a fraction of crotyl alcohol from said extract, and separating at least a fraction of said extractant from said raffinate to form an extractant-depleted raffinate.

Any form of extract separation from the raffinate is suitable. Typically, the extract is of lower specific gravity and could be separated by decantation. In a mixer-settler unit, separation takes place in the settler. In a column contactor, typically the extract exists near the top of the column and the raffinate near its bottom.

According to an embodiment, separating at least a fraction of crotyl alcohol from said extract comprises separating at least a fraction of said extractant from said extract to form an extractant-depleted crotyl alcohol solution and separated extractant. According to an embodiment, said separation of extractant from said extract comprises evaporation of the extractant, e.g. via pressure reduction and/or temperature elevation. According to an embodiment, at least 90% of the extractant in the extract is separated, at least 95%, at least 98%, at least 99% or at least 99.5%.

Separating extractant from said raffinate forms an extractant-depleted raffinate and separated extractant. According to an embodiment, said separation of extractant from said raffinate comprises evaporation of the extractant, e.g. via pressure reduction and/or temperature elevation. According to an embodiment, at least 90% of the extractant in the raffinate is separated, at least 95%, at least 98%, at least 99% or at least 99.5%.

According to an embodiment, the method further comprises liquefying at least a fraction of the separated extractant and said liquefying is driven by a refrigerant circuit. According to an embodiment, said liquefied extractant is reused in extracting.

According to an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

Crotyl Alcohol Refining

The extractant-depleted crotyl alcohol solution may comprise the majority of crotyl alcohol from the fermentation broth. According to an embodiment, due to the extractant selectivity, crotyl alcohol in said extractant-depleted crotyl alcohol solution is purer and more concentrated than in the fermentation broth.

According to an embodiment, the weight ratio between crotyl alcohol and water in said extractant-depleted crotyl alcohol solution is at least about 5 times greater than said ratio in said fermentation broth, at least 10 times, at least 15 times, at least 20 times, at least 25 times, at least 30 times, at least 40 times or at least 50 times greater.

According to an embodiment, the weight ratio between crotyl alcohol and water in said extractant-depleted crotyl alcohol solution is greater than said ratio in a saturated aqueous solution of crotyl alcohol at the same temperature. According to an embodiment, said extractant-depleted crotyl alcohol solution splits into two phases. One of those phases is enriched with crotyl alcohol, i.e. has a crotyl alcohol to water weight ratio greater than that in the extractant-depleted crotyl alcohol solution. Said crotyl alcohol-enriched phase is lighter than the other, which is crotyl alcohol depleted compared with the extractant-depleted crotyl alcohol solution. Accordingly, those phases are also referred to as "extract light phase" and "extract heavy phase," respectively.

According to an embodiment, the weight ratio between crotyl alcohol and water in said extract light phase is at least about 10 times greater than said ratio in said fermentation broth, at least 20 times, at least 30 times, at least 40 times, at least 50 times, at least 60 times, at least 70 times, at least 80 times, at least 90 times or at least 100 times greater.

According to an embodiment, crotyl alcohol is extracted selectively over said second bioproduct, but the extract also contains said second bioproduct. According to an embodiment, the weight ratio between crotyl alcohol and water in said extractant-depleted crotyl alcohol solution is greater than said ratio in a saturated aqueous solution of crotyl alcohol at the same temperature and said extractant-depleted crotyl alcohol solution splits into extract light phase and extract heavy phase. According to an embodiment, said second bioproduct distributes between said two phases. According to an embodiment, it distributes favorably into the extract heavy phase, i.e. its concentration in that heavy phase is greater than its concentration in the extract light phase. According to an embodiment the weight ratio between crotyl alcohol and said second bioproduct in said extract light phase is at least about 4 times greater than said ratio in said fermentation broth, at least 8 times greater, at least 12 times greater, at least 16 times greater, at least 20 times greater or at least 30 times greater.

According to these embodiments, the extractant-depleted crotyl alcohol solution, and even more so, the extract light phase contain crotyl alcohol at purity and concentration much higher than those in the fermentation broth. According to these embodiments, the extractant-depleted crotyl alcohol solution, the extract light phase or both are suitable for use as such and/or for conversion into downstream products, e.g. via enzymatic or chemical catalysis.

According to an embodiment, the method further comprises refining said extract light phase to further increase the purity and crotyl alcohol concentration of said extract light phase. According to an embodiment, said refining comprises, at least one of distillation, ion-exchange, crystallization, membrane separation, chromatographic separation, treatment with an absorbent, e.g. activated carbon, and combinations thereof.

According to an embodiment, the method further comprises refining said extract heavy phase, for the recovery of crotyl alcohol therein. According to an embodiment, the method further comprises refining said extract heavy phase, for the recovery of said second bioproduct. According to an embodiment, said extract heavy phase is combined with said broth prior to extraction or simultaneously with it. According to an embodiment, extraction uses an extraction column, said broth is introduced via a port near the bottom of the column and said extract heavy phase is introduced via a port at a somewhat higher location.

According to an embodiment, crotyl alcohol concentration in said broth is in the range between 1 wt % and 3 wt % and crotyl alcohol concentration in said extractant-depleted crotyl alcohol solution is at least about 15 wt %, at least 20 wt %, at least 25 wt %, at least 30 wt %, at least 35 wt %, at least 40 wt %, at least 45 wt % or at least 50 wt %.

According to an embodiment, said extractant-depleted crotyl alcohol solution splits into two phases, an extract light phase and an extract heavy phase. According to an embodiment, crotyl alcohol concentration in said extract light phase is at least about 45 wt %, at least 50 wt %, at least 55 wt %, at least 60 wt %, at least 65 wt %, at least 70 wt %, at least 75 wt % or at least 80 wt %. According to an embodiment, crotyl alcohol concentration in said extract heavy phase is less than about 20 wt %, less than 15 wt %, less than 12 wt %, less than 10 wt %, less than 8 wt % or less than 7 wt %.

According to an embodiment, said second bioproduct is selected from the group consisting of ethanol, isopropanol, acetone, a carboxylic acid and their combinations. According to an embodiment, said extractant-depleted crotyl alcohol solution splits into two phases and said second bioproduct distributes between the two phases. According to an embodiment, it distributes favorably into the extract heavy phase, i.e. its concentration in that heavy phase is greater than its concentration in the extract light phase. According to an embodiment, the concentration of said second bioproduct in said fermentation broth is in the range between 0.05 and 10 g/L, its concentration in the extract light phase is in the range between 0.1 and 50 g/L and/or its concentration in the extract heavy phase is in the range between 50 and 400 g/L.

According to an embodiment, said second bioproduct comprises ethanol and acetone and said extract light phase is refined by distillation. According to an embodiment, said distillation forms a refined crotyl alcohol product, an ethanol product and an acetone product. According to an embodiment, said the purity of said refined crotyl alcohol product is greater than 98 wt %, greater than 99 wt %, greater than 99.5 wt %, greater than 99.8 wt % or greater than 99.0 wt %.

According to an embodiment, said refined crotyl alcohol product is used as such, e.g. as fuel additive. Additionally or alternatively, said method further comprises converting said crotyl alcohol into a further product. According to an embodiment, said further product is selected from jet fuel and butadiene. According to an embodiment, said converting comprises chemical catalysis. According to an embodiment, said converting comprises dehydration.

Raffinate Recycling

Said separating extractant from said raffinate generates an extractant-depleted raffinate. According to an embodiment, said extractant-depleted raffinate may comprise a carbon source and a nitrogen source. According to an embodiment, the concentration of said carbon source in said extractant-depleted raffinate is in a range between 0.1 and 20 g/L. According to an embodiment, the concentration of said nitrogen source in said extractant-depleted raffinate is in a range between 0.1 and 5 g/L. According to an embodiment, it comprises residual crotyl alcohol and optionally at least one second bioproducts.

The method of the third aspect comprises mixing at least a fraction of said extractant-depleted raffinate with a carbon source and a nitrogen source to form said fermentation medium. Differently put, at least a fraction of said extractant-depleted raffinate is recycled to fermentation.

The extractant has high selectivity to crotyl alcohol over the nutrients components of the fermentation broth, such as the carbon source, the nitrogen source, vitamins and minerals. According to an embodiment, extractant to broth flux ratio is selected so that, while crotyl alcohol extraction yield is high, that of those nutrients is low. According to an embodiment, less than 10% of the nutrients co-extract with crotyl alcohol, less than 8%, less than 6%, less than 4%, less than 2% or less than 1%. As a result, more than 90% of those nutrients remain in the extractant-depleted raffinate, more than 92%, more than 94%, more than 96%, more than 98% or more than 99%. Recycling at least a fraction of said extractant-depleted raffinate to the fermentation medium leads therefore to major savings.

According to an embodiment, said extractant-depleted raffinate comprises ethanol at a concentration between 1 and 15 g/L and acetone at a concentration between 0.5 and 10 g/L. According to an embodiment, the concentration of ethanol and acetone in the fermentation broth is greater than that in the extractant-depleted raffinate.

According to an embodiment, said recycled extractant-depleted raffinate comprises residual amounts of said extractant, e.g. less than 1000 ppm extractant, less than 500 ppm, less than 100 ppm or less than 50 ppm. According to an embodiment, at least a fraction of said extractant evaporates during said fermenting. Optionally said extractant removal is facilitated by gaseous coproducts of fermentation, e.g. $CO_2$.

According to an embodiment, a fraction of said extractant-depleted raffinate is purged prior to said recycling in order to maintain an acceptable steady state concentration of impurities therein.

According to various embodiments, the method of the third aspect is characterized by selecting an extractant and extractant/broth ratio that lead to high crotyl alchol extraction yields, but low yields on extraction of other components so that these other components remain in the raffinate; by using said raffinate to form the fermentation medium of the next cycle, by the relatively high concentration of fermentation coproduct (carboxylic acid, ethanol and/or acetone) in said fermentation medium; by resulting extractant concentration in the fermentation medium and by efficient fermentation in the medium comprising said coproducts and extractant.

EXAMPLES

Examples 1-9: Extraction of Various Bioproducts with 1-Butene 100 g (grams) aqueous solutions of various bioproducts were prepared. Bioproduct initial concentration was 2%. Each of these bioproduct aqueous solutions was extracted in a pressure vessel by mixing with 100 g 1-butene (the olefin). The amount of formed extract and formed raffinate and the concentration (conc.) of the bioproduct in each were determined. Theses concentrations were used to calculate the bioproduct distribution coefficient (DC). The results are summarized in Table 1. Table 2 compares the found distribution coefficients to those of extracting with dimethyl ether (DME).

TABLE 1

| | | Extract | | Raffinate | | |
| --- | --- | --- | --- | --- | --- | --- |
| Example # | Bioproduct | Amount (g) | Bioproduct conc. (%) | Amount (g) | Bioproduct conc. (%) | DC |
| 1 | 2-Pentanone | 97.5 | 1.81 | 102.4 | 0.23 | 7.95 |
| 2 | Butanal | 97.5 | 1.78 | 102.5 | 0.26 | 6.96 |
| 3 | Butanol | 96.6 | 1.02 | 103.4 | 0.98 | 1.04 |
| 4 | Furfural | 97.3 | 1.56 | 102.7 | 0.47 | 3.35 |
| 5 | Gamma Butyrolactone | 97.3 | 1.60 | 102.7 | 0.43 | 3.69 |
| 6 | Glutaric Acid | 96.0 | 0.44 | 104.00.23 | 1.51 | 0.27 |
| 7 | Methyl Butyrate | 97.8 | 2.00 | 102.2 | 0.038 | 53.8 |
| 8 | Propionic Acid | 96.6 | 1.00 | 103.3 | 1.00 | 1.01 |
| 9 | Succinic Acid | 95.7 | 0.158 | 104.3 | 1.77 | 0.11 |

TABLE 2

| Compound | Distribution coefficient | |
|---|---|---|
| | 1-butene | DME |
| 2-Pentanone | 7.95 | 5.82 |
| Butanal | 6.96 | 5.11 |
| Butanol | 1.04 | 2.92 |
| Furfural | 3.35 | 3.79 |
| Gamma Butyrolactone | 3.69 | 3.14 |
| Glutaric Acid | 0.27 | 1.88 |
| Methyl Butyrate | 53.8 | 20.73 |
| Propionic Acid | 1.01 | 2.27 |
| Succinic Acid | 0.11 | 1.01 |

Extracting most of the biomolecules, with 1-butene, shows relatively high distribution coefficients confirming high extraction yields at relatively low extractant to biomolecules solution flux ratios. Dicarboxylic acids, particularly the lower molecular weight ones, are more difficult to extract.

As shown in Table 2, for many of the tested bioproducts, the distribution coefficient of extracting with 1-butene is quite similar to that of extracting with DME.

Example 10: Energy Consumption

An Aspen model was created for counter-current extraction of n-butanol from its fermentation broth in a multiple stage extraction column. The pressure of both the broth and the extractant are kept above the vapor pressure of the extractant at 37° C. This produces an n-butanol-lean raffinate and an n-butanol-enriched extract. The extract is sent to a heater and subsequent flash tank in which the extractant is removed from the extract. The raffinate is also sent to a heater and subsequent flash tank.

Two extractants were compared: (i) 1-butene (the olefin) and (ii) DME. The extraction parameters were adjusted so that the yield for both extractants are nearly the same. The energy required to decrease the concentration of the extractant in the raffinate was then calculated in Aspen.

The recovery scheme first involves a pressure let-down to near ambient conditions. This is done to decrease the vapor pressure of the raffinate, thus providing more favorable conditions for evaporation of the extractant out of the raffinate stream. Then the raffinate is heated. The raffinate then enters a flash tank, where evolved vapor separate from the liquid. This vapor is collected and compressed back to the starting pressure, i.e. above the vapor pressure of the solvent at 37° C. The process of compressing the extractant increases its temperature, which allows for the transfer of its energy for heating the depressurized raffinate. This also partially or fully condenses the extractant, which can be reused in the counter-current extraction column. This scheme represents an efficient way of saving on operating expenditures.

Table 3 summarizes the energy requirements for these extractant compositions normalized for the amount of butanol extracted in the column. The table also indicates the number of equilibrium stages of each extraction column, as well as the heat exchange (HX) duty (which provides an indication for how large the potential heat exchanger may be).

TABLE 3

| | Units | Dimethyl-Ether (DME) | 1-Butene |
|---|---|---|---|
| Wt % Solvent in Raffinate | | 31.4% | 4.7% |
| % Extracted | | 91.99% | 88.99% |
| # of stages | | 3 | 7 |
| HX Duty/BuOH | MBtu/lb* | 8.42 | 0.31 |
| Electricity/BuOH | kWh/lb** | 0.663 | 0.026 |

*MBtu/lb = One million British thermal units per pound.
**kWh/lb = kilowatt hours per pound These data suggest that at about the same extraction yield, despite requiring a smallest number of equilibrium stages, the DME needs more electrical energy and a larger heat exchanger than 1-butene.

The invention claimed is:

1. A method for producing a bioproduct comprising:
   (i) mixing a carbon source and a nitrogen source to form a fermentation medium;
   (ii) fermenting said medium with a microorganism to form a fermentation broth containing at least one bioproduct;
   (iii) extracting at least a fraction of said fermentation broth with an extractant comprising an olefin to form an extract and a raffinate, wherein both extract and raffinate comprise said extractant, said bioproduct, and water; and wherein the boiling point of said olefin at atmospheric pressure is under 10° C.;
   (iv) separating said extract from said raffinate;
   (v) separating at least a fraction of the bioproduct from said extract, wherein said separating comprises separating at least a fraction of said extractant from said extract to form an extractant-depleted bioproduct solution;
   (vi) separating at least a fraction of said extractant from said raffinate to generate an extractant-depleted raffinate; and
   (vii) liquefying at least a fraction of the separated extractant with a refrigerant in a refrigerant circuit, wherein the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia,
   wherein said bioproduct comprises crotyl alcohol in combination with one or more of butanol, ethanol, acetone, isopropanol, a carboxylic acid, or combinations thereof.

2. The method according to claim 1, wherein said fermentation medium further comprises at least a fraction of an extractant-depleted raffinate and wherein said fermentation medium further comprises said extractant.

3. The method according to claim 1, wherein said butanol is n-butanol.

4. The method according to claim 1, wherein said carboxylic acid is butyric acid.

5. The method according to claim 1, wherein said olefin is selected from the group consisting of 1-butene, 2-butene, and iso-butene.

6. The method according to claim 1, wherein said fermentation broth further comprises at least one additional bioproduct which is selected from the group consisting of ethanol, acetone, isopropanol, and a carboxylic acid.

7. The method according to claim 1, wherein the concentration of said bioproduct in said fermentation broth is less than 5 wt %.

8. The method according to claim 1, wherein said fermentation broth contains cell mass during said extracting.

9. The method according to claim 1, wherein said extractant further comprises at least one of dimethyl ether, methylethyl ether, and diethyl ether.

10. The method according to claim 1, wherein the weight ratio between bioproduct and water in said extract is at least 5 times greater than said ratio in said fermentation broth.

11. The method according to claim 1, wherein the weight ratio between bioproduct and water in said extract is greater than said ratio in a saturated aqueous solution of said bioproduct at the same temperature.

12. The method according to claim 1, wherein both said fermentation broth and said extract contain a second bioproduct, and wherein the weight ratio between said bioproduct and said second bioproduct in said extract is at least 2 times greater than said ratio in said fermentation broth.

13. The method according to claim 1, wherein both said fermentation broth and said extract contain a carbon source, and wherein the weight ratio between said bioproduct and said carbon source in said extract is at least 10 times greater than said ratio in said fermentation broth.

14. The method according to claim 1, wherein both said fermentation broth and said extract contain a nitrogen source, and wherein the weight ratio between said bioproduct and said nitrogen source in said extract is at least 10 times greater than said ratio in said fermentation broth.

15. The method according to claim 1, wherein said extracting is conducted in a counter-current column, wherein the extractant to fermentation broth flux ratio is in the range between 0.5 and 5, and wherein at least 80% of the bioproduct in said fermentation broth is extracted; wherein said fermentation broth contains a second bioproduct, wherein said extracting further comprises extracting a fraction of said second bioproduct, and wherein the extracted fraction of said second bioproduct is smaller than the fraction of extracted bioproduct.

16. The method according to claim 1, wherein said microorganism is viable in a fermentation broth comprising said extractant at a concentration of at least 0.01 g/L.

17. The method according to claim 1, wherein said microorganism is a member of the phylum Firmicutes, a member of the class Clostridia, a member of the genus *Eubacterium*, a member of the genus *Clostridium* or is a *Eubacterium limosum*.

18. The method according to claim 1, wherein said microorganism is a *Clostridium* selected from the group consisting of *Clostridium butyricum, Clostridium acetobutylicum, Clostridium saccharoperbutylacetonicum, Clostridium butyricum, Clostridium saccharobutylicum, Clostridium pasteurianum, Clostridium kluyveri, Clostridium carboxidovorans, Clostridium phytofermentens, Clostridium thermocellum, Clostridium cellulolyticum, Clostridium cellulovorans, Clostridium clariflavum, Clostridium ljungdahlii, Clostridium acidurici, Clostridium tyrobutyricum*, and *Clostridium autoethanogenum*.

19. The method according to claim 1, wherein said carboxylic acid is selected from the group consisting of acetic acid, butyric acid, and lactic acid.

20. The method according to claim 1, wherein said carbon source comprises liquefied corn, the fermentation broth additionally contains wet solids, the method further comprises separating at least a fraction of wet solids from said fermentation broth and contacting said wet solids with a fraction of said extractant-depleted raffinate to form a mixture and separating bioproduct from said mixture to form a bioproduct-depleted residue.

21. The method according to claim 1, wherein said bioproduct further comprises one or more alcohols, carboxylic acids, hydroxycarboxylic acids, dicarboxylic acids, furfurals, ketones, aldehydes, esters, lactones, lipids, glycolipids, carotenoids, polysaccharides or combinations thereof.

* * * * *

UNITED STATES PATENT AND TRADEMARK OFFICE
CERTIFICATE OF CORRECTION

PATENT NO. : 10,612,051 B2
APPLICATION NO. : 15/563190
DATED : April 7, 2020
INVENTOR(S) : Tracy et al.

It is certified that error appears in the above-identified patent and that said Letters Patent is hereby corrected as shown below:

In the Claims

Column 40, Line 15 (Claim 18) please change "*Clostridium butyricum*" to -- *Clostridum beijerickii* --

Signed and Sealed this
Seventeenth Day of November, 2020

Andrei Iancu
*Director of the United States Patent and Trademark Office*